US012653649B2

(12) United States Patent
Knudby et al.

(10) Patent No.: US 12,653,649 B2
(45) Date of Patent: Jun. 16, 2026

(54) GENERATION OF A THREE-DIMENSIONAL REPRESENTATION OF A DENTAL OBJECT DURING SCANNING WITH A DENTAL IMAGING DEVICE

(71) Applicant: 3SHAPE A/S, Copenhagen K (DK)

(72) Inventors: Søren Knudby, Copenhagen K (DK); Henrik Aanæs, Copenhagen K (DK); Henrik Öjelund, Copenhagen K (DK); Marek Krzysztof Misztal, Copenhagen K (DK)

(73) Assignee: 3Shape A/S, Kobenhavn K (DK)

( * ) Notice: Subject to any disclaimer, the term of this patent is extended or adjusted under 35 U.S.C. 154(b) by 543 days.

(21) Appl. No.: 18/181,613

(22) Filed: Mar. 10, 2023

(65) Prior Publication Data

US 2023/0293271 A1     Sep. 21, 2023

(30) Foreign Application Priority Data

Mar. 17, 2022     (EP) ..................................... 22162665

(51) Int. Cl.
| | |
|---|---|
| *G06T 3/14* | (2024.01) |
| *A61B 1/00* | (2006.01) |

(Continued)

(52) U.S. Cl.
CPC .............. *A61C 9/0053* (2013.01); *A61B 1/24* (2013.01); *G06T 2207/10* (2013.01)

(58) Field of Classification Search
None
See application file for complete search history.

(56) References Cited

U.S. PATENT DOCUMENTS

| | | | |
|---|---|---|---|
| 9,286,682 B1 * | 3/2016 | Carr | ......................... G06T 7/337 |
| 11,076,146 B1 | 7/2021 | Fisker et al. | |

(Continued)

FOREIGN PATENT DOCUMENTS

| | | |
|---|---|---|
| WO | 0216867 A1 | 2/2002 |
| WO | 2010048960 A1 | 5/2010 |

(Continued)

OTHER PUBLICATIONS

S. Chen, "Intraoral 3-D Measurement by Means of Group Coding Combined With Consistent Enhancement for Fringe Projection Pattern," in IEEE Transactions on Instrumentation and Measurement, vol. 71, pp. 1-12, 2022, Art No. 5018512, doi: 10.1109/TIM. 2022.3197782. (Year: 2022).*

(Continued)

*Primary Examiner* — Beniyam Menberu
(74) *Attorney, Agent, or Firm* — BUCHANAN INGERSOLL & ROONEY PC

(57)     ABSTRACT

The present disclosure relates to a computer-implemented method for improving the accuracy of a digital three-dimensional representation of a dental object during scanning, the method comprising the steps of: generating a digital three-dimensional (3D) representation of the dental object based on registration and stitching of a plurality of 3D scan patches; obtaining new 3D scan patches in real-time during scanning; registering said new 3D scan patches to the digital 3D representation during scanning, whereby said scan patches form part of the digital 3D representation; selecting a sub-set of 3D scan patches among the obtained or registered 3D scan patches, wherein said selection is performed during scanning; and re-registering one or more 3D scan patches forming part of the digital 3D representation, wherein said re-registering is based on applying one or more transformations to the selected sub-set of scan patches, (Continued)

whereby the accuracy of a digital 3D representation is improved.

19 Claims, 11 Drawing Sheets

(51) Int. Cl.

| | | |
|---|---|---|
| *A61B 1/24* | (2006.01) | |
| *A61C 9/00* | (2006.01) | |
| *G06T 19/20* | (2011.01) | |

(56) References Cited

U.S. PATENT DOCUMENTS

| | | | |
|---|---|---|---|
| 2009/0061381 A1 | 3/2009 | Durbin | |
| 2013/0286174 A1* | 10/2013 | Urakabe | A61B 1/04 |
| | | | 348/66 |
| 2013/0329020 A1 | 12/2013 | Kriveshko | |
| 2018/0296080 A1* | 10/2018 | Glinec | A61B 1/24 |
| 2018/0360317 A1 | 12/2018 | Fisker | |
| 2018/0367786 A1* | 12/2018 | Furst | G01J 3/0264 |
| 2020/0349705 A1 | 11/2020 | Minchenkov et al. | |
| 2021/0059796 A1 | 3/2021 | Weiss | |
| 2022/0110723 A1* | 4/2022 | Raby | A61C 7/002 |
| 2022/0192800 A1* | 6/2022 | Koza | A61B 1/00172 |
| 2022/0202382 A1* | 6/2022 | Elvers | G06T 7/0012 |
| 2023/0030807 A1* | 2/2023 | Pollard | G06F 30/10 |
| 2023/0042643 A1* | 2/2023 | Saphier | A61C 9/0046 |

FOREIGN PATENT DOCUMENTS

| | | |
|---|---|---|
| WO | 2010145669 A1 | 12/2010 |
| WO | 2012083967 A1 | 6/2012 |
| WO | 2012168322 A2 | 12/2012 |
| WO | 2013010910 A1 | 1/2013 |
| WO | 2013132091 A1 | 9/2013 |
| WO | 2014000745 A1 | 1/2014 |
| WO | 2014125037 A1 | 8/2014 |
| WO | 2018172257 A1 | 9/2018 |
| WO | 2020148041 A1 | 7/2020 |

OTHER PUBLICATIONS

J. Wang et al., "Augmented Reality Navigation With Automatic Marker-Free Image Registration Using 3-D Image Overlay for Dental Surgery," in IEEE Transactions on Biomedical Engineering, vol. 61, No. 4, pp. 1295-1304, Apr. 2014, doi: 10.1109/TBME.2014.2301191 (Year: 2014).*

The extended European Search Report issued on Aug. 1, 2023, by the European Patent Office in corresponding European Application No. 23161109.6. (8 pages).

* cited by examiner

3D Object Representations 134

Master 3D Representation
134a

Registration 3D Representation
134b

Visualization 3D Representation
134c

Space Exclusion 3D Representation
134d

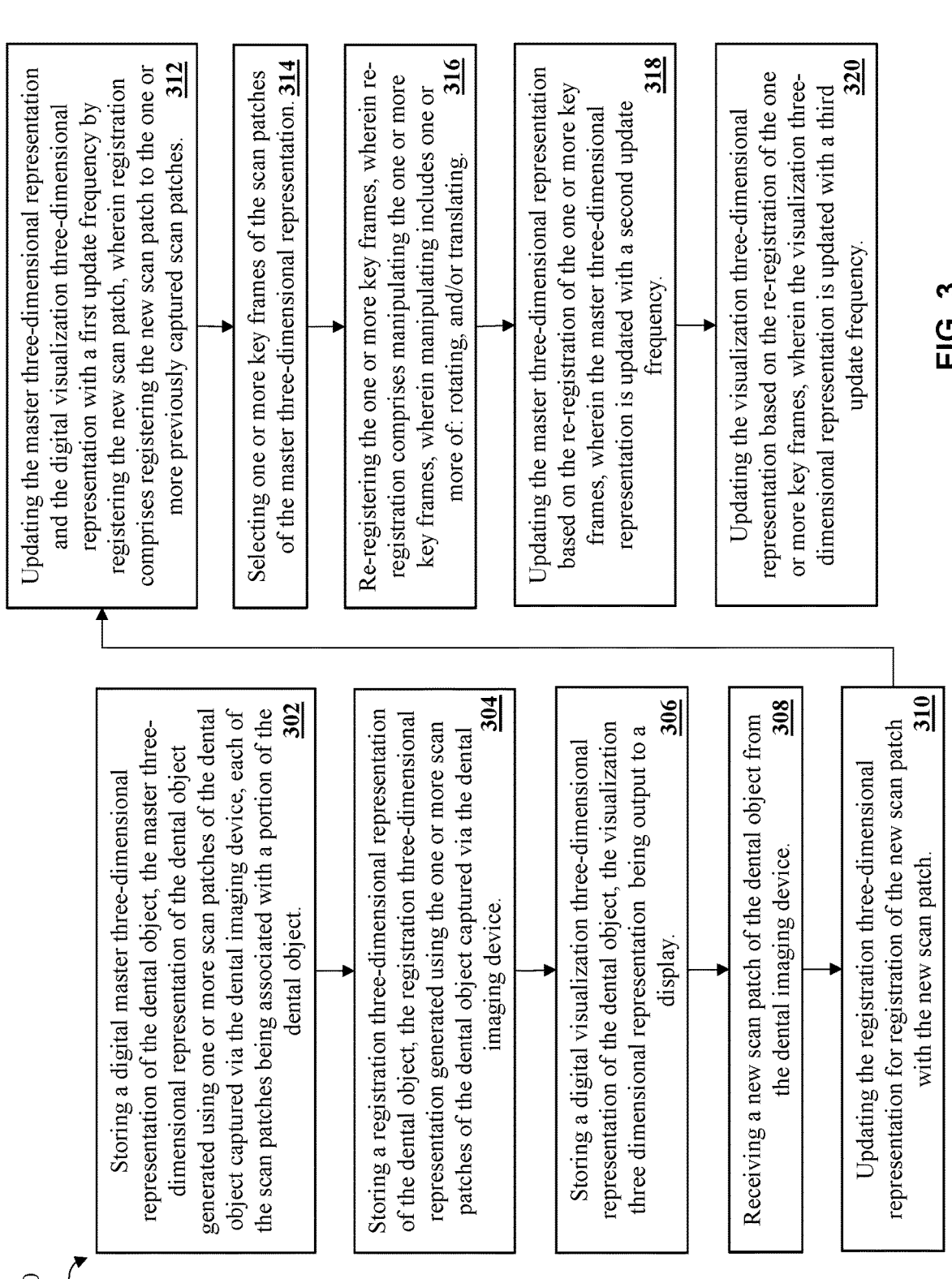

Storing a digital master three-dimensional representation of the dental object, the master three-dimensional representation of the dental object generated using one or more scan patches of the dental object captured via the dental imaging device, each of the scan patches being associated with a portion of the dental object.          302

Storing a registration three-dimensional representation of the dental object, the registration three-dimensional representation generated using the one or more scan patches of the dental object captured via the dental imaging device.          304

Storing a digital visualization three-dimensional representation of the dental object, the visualization three dimensional representation being output to a display.          306

Receiving a new scan patch of the dental object from the dental imaging device.          308

Updating the registration three-dimensional representation for registration of the new scan patch with the new scan patch.          310

Updating the master three-dimensional representation and the digital visualization three-dimensional representation with a first update frequency by registering the new scan patch, wherein registration comprises registering the new scan patch to the one or more previously captured scan patches.          312

Selecting one or more key frames of the scan patches of the master three-dimensional representation.          314

Re-registering the one or more key frames, wherein re-registration comprises manipulating the one or more key frames, wherein manipulating includes one or more of: rotating, and/or translating.          316

Updating the master three-dimensional representation based on the re-registration of the one or more key frames, wherein the master three-dimensional representation is updated with a second update frequency.          318

Updating the visualization three-dimensional representation based on the re-registration of the one or more key frames, wherein the visualization three-dimensional representation is updated with a third update frequency.          320

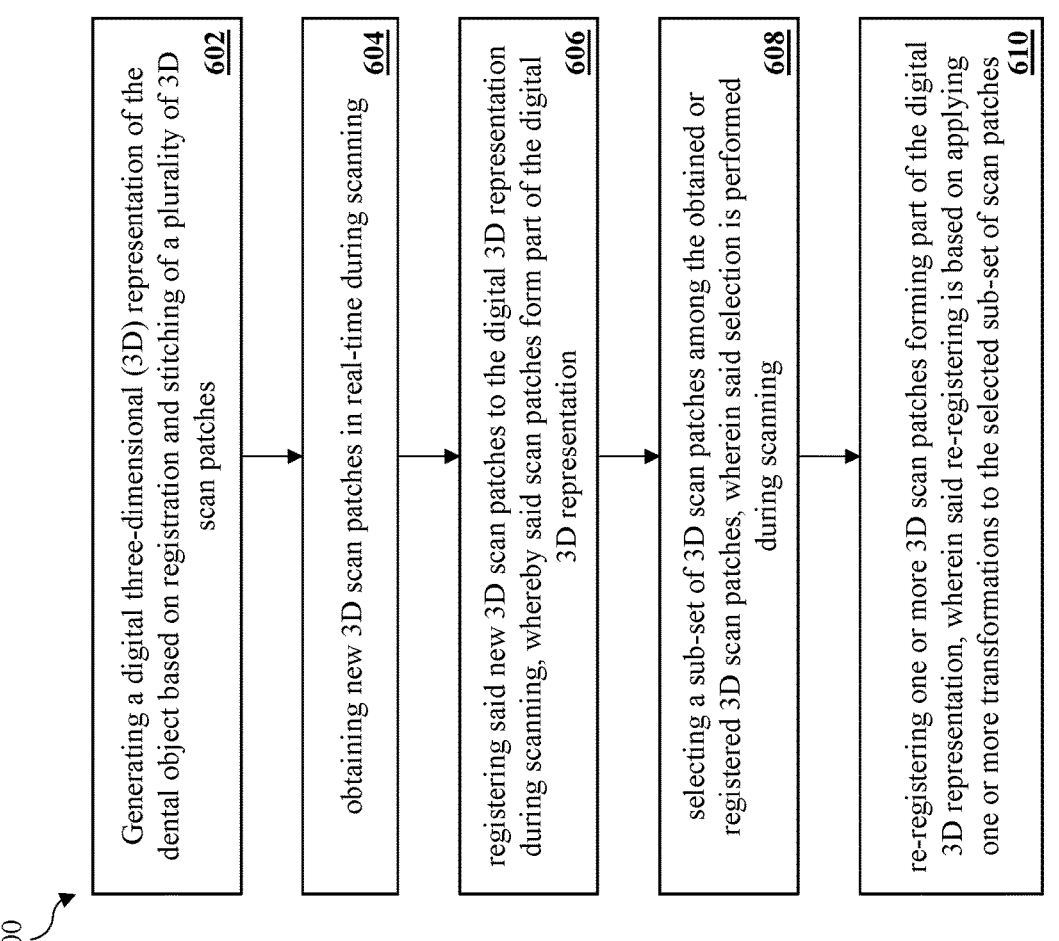

Generating a digital three-dimensional (3D) representation of the dental object based on registration and stitching of a plurality of 3D scan patches          602 obtaining new 3D scan patches in real-time during scanning          604 registering said new 3D scan patches to the digital 3D representation during scanning, whereby said scan patches form part of the digital 3D representation          606 selecting a sub-set of 3D scan patches among the obtained or registered 3D scan patches, wherein said selection is performed during scanning          608 re-registering one or more 3D scan patches forming part of the digital 3D representation, wherein said re-registering is based on applying one or more transformations to the selected sub-set of scan patches          610

GENERATION OF A THREE-DIMENSIONAL REPRESENTATION OF A DENTAL OBJECT DURING SCANNING WITH A DENTAL IMAGING DEVICE

TECHNICAL FIELD

The present disclosure relates to methods, systems, and computer program products for configuring a computer for generating a digital three-dimensional representation of a dental object during scanning with a dental imaging device. More particularly, the present disclosure relates to the real-time accurate generation of a three-dimensional representation of a patient's oral cavity while that oral cavity is being scanned by a dental imaging device.

BACKGROUND

In traditional dentistry, the dentist makes a physical dental impression of a patient's teeth when the patient needs a crown, a bridge, a denture, a removable, or an orthodontic treatment etc. An impression is carried out by placing a viscous liquid material into the mouth, usually in a dental impression tray. The material, usually an alginate, then sets to become an elastic solid, and, when removed from the mouth, provides a detailed and stable reproduction of teeth. When the impression is made, cheek retractors are arranged in the patient's mouth to avoid having the soft movable cheeks affect the impression of the teeth. Today direct three-dimensional scanning of the patient's teeth can be obtained using an intraoral handheld three-dimensional scanner instead of making a physical dental impression. An intraoral handheld three-dimensional scanner provides scan patches of 2.5-dimensional data or 3-dimensional data, such as data containing depth maps and/or color, of the patient's oral cavity. A three-dimensional reconstruction system sequentially builds a three-dimensional model of the patient's oral cavity by stitching the scan patches together in the order in which they are provided by the scanner. Before stitching a scan patch, the three-dimensional reconstruction system first performs a three-dimensional localization, i.e., registration, of the scan patch on the existing partially reconstructed three-dimensional model. Existing systems and methods for reconstructing a three-dimensional model typically include a post-processing step after the scanning has stopped. This step serves as an optimization step, wherein individual scan patches of the model are relocated and/or removed to improve the accuracy of the model. However, such an optimization step is not feasible in real-time because the computation time increases with the total number of scan patches.

Therefore, it is of interest to develop a new method for improving the accuracy of a three-dimensional model, wherein said method can be performed in real-time, i.e. during the scanning. In some cases, if the hand-held scanner is moved in certain scan paths, e.g. where loops occur, the registration and reconstruction steps become more challenging, and may consequently lead to an inaccurate three-dimensional model. Currently, a known solution for correcting such inaccuracies involves an optimization step, as explained above, which is executed after scanning has stopped. Therefore, current methods typically assume that previous scan patches do not change until after scanning is stopped. Thus, there is a need for a novel solution to more accurately and effectively generate a three-dimensional model of a patient's oral cavity.

SUMMARY

A method for generating a digital three-dimensional representation of a dental object during scanning with a dental imaging device is disclosed. In particular, the present disclosure relates to a computer-implemented method for improving the accuracy of a digital three-dimensional representation of a dental object during scanning. According to some embodiments of the disclosure, the method comprises the steps of generating a digital three-dimensional (3D) representation of the dental object based on registration and stitching of a plurality of 3D scan patches; obtaining new 3D scan patches in real-time during scanning; registering said new 3D scan patches to the digital 3D representation during scanning, whereby said scan patches form part of the digital 3D representation; selecting a sub-set of 3D scan patches among the obtained or registered 3D scan patches, wherein said selection is performed during scanning; and re-registering one or more 3D scan patches forming part of the digital 3D representation, wherein said re-registering is based on applying one or more transformations to the selected sub-set of scan patches, whereby the accuracy of a digital 3D representation is improved.

According to some embodiments of the disclosure, the method includes storing a digital master three-dimensional representation of the dental object, the digital master three-dimensional representation of the dental object generated using one or more scan patches of the dental object captured via the dental imaging device, each of the scan patches being associated with a portion of the dental object; storing a digital registration three-dimensional representation of the dental object, the digital registration three-dimensional representation generated using the one or more scan patches of the dental object captured via the dental imaging device; storing a digital visualization three-dimensional representation of the dental object, the visualization three-dimensional representation being output to a display; receiving a new scan patch of the dental object from the dental imaging device; updating the digital registration three-dimensional representation for registration of the new scan patch with the new scan patch; updating the digital master three-dimensional representation and the digital visualization three-dimensional representation with a first update frequency by registering the new scan patch, wherein registration comprises registering the new scan patch to the one or more previously captured scan patches; selecting one or more key frames of the scan patches of the digital master three-dimensional representation; re-registering the one or more key frames, wherein re-registration comprises manipulating the one or more key frames, wherein manipulating includes one or more of: rotating, and/or translating; updating the digital master three-dimensional representation based on the re-registration of the one or more key frames, wherein the digital master three-dimensional representation is updated with a second update frequency; and updating the digital visualization three-dimensional representation based on the re-registration of the one or more key frames, wherein the digital visualization three-dimensional representation is updated with a third update frequency. In the present context, the terms 'manipulating' and 'applying one or more transformations' are used interchangeably. A transformation may be understood as a geometric transformation, such as an affine transformation. In particular, the transformation(s) may include one or more of translation, rotation, and/or combinations thereof.

A system for generating a digital three-dimensional representation of a dental object during scanning with a dental imaging device is disclosed. The system may include a memory of a processing device configured to: store a digital master three-dimensional representation of the dental object, the digital master three-dimensional representation of the dental object generated using one or more scan patches of the dental object captured via the dental imaging device, each of the scan patches being associated with a portion of the dental object; store a digital registration three-dimensional representation of the dental object, the digital registration three-dimensional representation generated using the one or more scan patches of the dental object captured via the dental imaging device; store a digital visualization three-dimensional representation of the dental object, the visualization three-dimensional representation being output to a display; a processor of the processing device configured to: receive a new scan patch of the dental object from the dental imaging device; update the digital registration three-dimensional representation for registration of the new scan patch with the new scan patch; update the digital master three-dimensional representation and the digital visualization three-dimensional representation with a first update frequency by registering the new scan patch, wherein registration comprises registering the new scan patch to the one or more previously captured scan patches; select one or more key frames of the scan patches of the digital master three-dimensional representation; re-register the one or more key frames, wherein re-registration comprises manipulating the one or more key frames, wherein manipulating includes one or more of: rotating, and/or translating; update the digital master three-dimensional representation based on the re-registration of the one or more key frames, wherein the digital master three-dimensional representation is updated with a second update frequency; and update the digital visualization three-dimensional representation based on the re-registration of the one or more key frames, wherein the digital visualization three-dimensional representation is updated with a third update frequency.

A computer program product for generating a digital three-dimensional representation of a dental object during scanning with a dental imaging device is disclosed. The computer program product may include: a computer-readable storage medium having program instructions embodied therewith, the program instructions executable by a computer to cause the computer to perform any of the methods disclosed herein, such as the method comprising the steps of: storing a digital master three-dimensional representation of the dental object, the digital master three-dimensional representation of the dental object generated using one or more scan patches of the dental object captured via the dental imaging device, each of the scan patches being associated with a portion of the dental object; storing a digital registration three-dimensional representation of the dental object, the digital registration three-dimensional representation generated using the one or more scan patches of the dental object captured via the dental imaging device; storing a digital visualization three-dimensional representation of the dental object, the visualization three-dimensional representation being output to a display; receiving a new scan patch of the dental object from the dental imaging device; updating the digital registration three-dimensional representation for registration of the new scan patch with the new scan patch; updating the digital master three-dimensional representation sentation and the digital visualization three-dimensional representation with a first update frequency by registering the new scan patch, wherein registration comprises registering the new scan patch to the one or more previously captured scan patches; selecting one or more key frames of the scan patches of the digital master three-dimensional representation; re-registering the one or more key frames, wherein re-registration comprises manipulating the one or more key frames, wherein manipulating includes one or more of: rotating, and/or translating; updating the digital master three-dimensional representation based on the re-registration of the one or more key frames, wherein the digital master three-dimensional representation is updated with a second update frequency; and updating the digital visualization three-dimensional representation based on the re-registration of the one or more key frames, wherein the digital visualization three-dimensional representation is updated with a third update frequency.

The re-registration may include translating and/or rotating one or more 3D scan patches, such as the previously registered 3D scan patches, relative to each other or relative to the digital 3D representation. Although the presently disclosed method has been described using three digital three-dimensional representations: a master-, a registration-, and a visualization-representation, the disclosed method is not limited to the usage of three distinct representations. Instead, the method may utilize (such as generate, store, retrieve, and/or update) one representation, generally referred to as a digital three-dimensional representation. Thus, in some embodiments, there is no distinction between a registration representation and a master representation. In general, the method may employ any one or more of the aforementioned digital representations.

BRIEF DESCRIPTION OF THE DRAWINGS

The scope of the present disclosure is best understood from the following detailed description of exemplary embodiments when read in conjunction with the accompanying drawings. Included in the drawings are the following figures:

FIG. 10 illustrates an example system for generating a digital three-dimensional representation of a dental object during scanning with a dental imaging device in accordance with exemplary embodiments;

FIG. 3 is a flowchart illustrating a method for generating a digital three-dimensional representation of a dental object during scanning with a dental imaging device in accordance with exemplary embodiments;

FIG. 6 is a flowchart illustrating a method for generating a digital three-dimensional representation of a dental object during scanning with a dental imaging device in accordance with exemplary embodiments.

DETAILED DESCRIPTION

As discussed above, current methods and technologies in the realm of three-dimensional reconstruction of an oral cavity can produce an inaccurate three-dimensional model when scanning the oral cavity with a three-dimensional intraoral scanner, which can then affect the ability to correctly register subsequent scan patches of the oral cavity. Exemplary embodiments of the methods and systems provided herein address the issues with the current methods and technologies by allowing scan patches to be re-registered after their initial registration based on knowledge from subsequent scan patches.

The disclosed method may include the step of re-registering one or more 3D scan patches forming part of the digital 3D representation, wherein said re-registering is based on applying one or more transformations to a selected sub-set of scan patches, whereby the accuracy of a digital 3D representation is improved. An advantage of applying the transformation(s) to a selected sub-set is a reduction in the needed computational costs (e.g. in terms of power and time) compared to applying the transformation(s) to all of the scan patches. Advantageously, scan patches not forming part of the selected sub-set may subsequently (e.g. doing a re-registration step) be transformed based on the applied transformation(s) to nearby scan patches which are included in the sub-set, such as based on a weighted average of said applied transformation(s).

Thus, exemplary embodiments of the methods and systems provided herein provide a more accurate three-dimensional model, a better scanning experience for both inexperienced and experienced users alike. For example, the methods and systems provided herein provide a better scanning experience for inexperienced and experienced users because the improved system is more robust to different scan paths and/or less dependent on the chosen scan path. Further, exemplary embodiments of the methods and systems provided herein introduce several three-dimensional representations representing the same reconstructed surface/object but having different purposes and allowing the re-registration of scan patches during the real-time reconstruction.

Figure 1A:
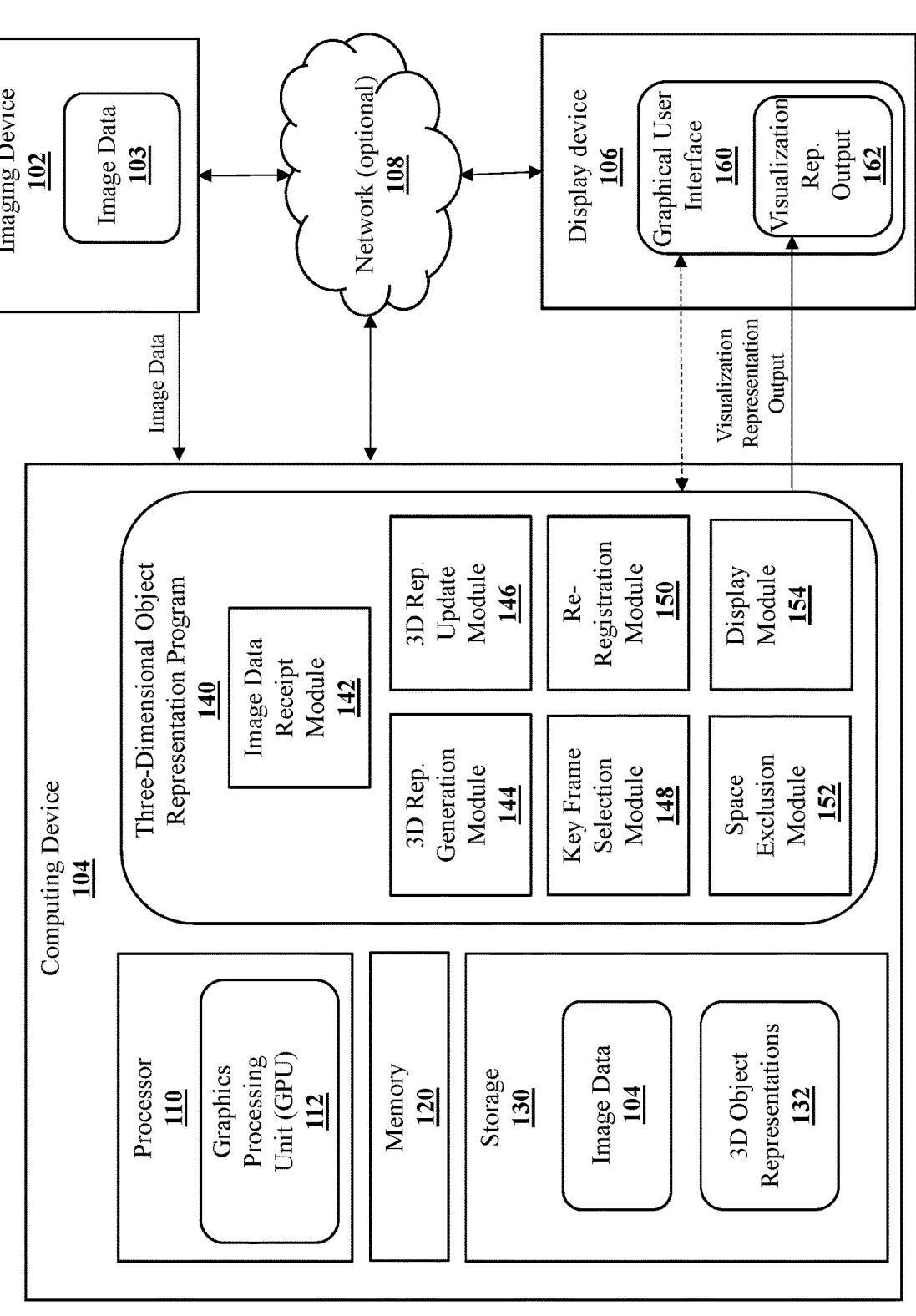
FIG. 1A illustrates a high-level system architecture for configuring a computer for generating a digital three-dimensional representation of a dental object during scanning with a dental imaging device in accordance with exemplary embodiments.
Figure 1B:
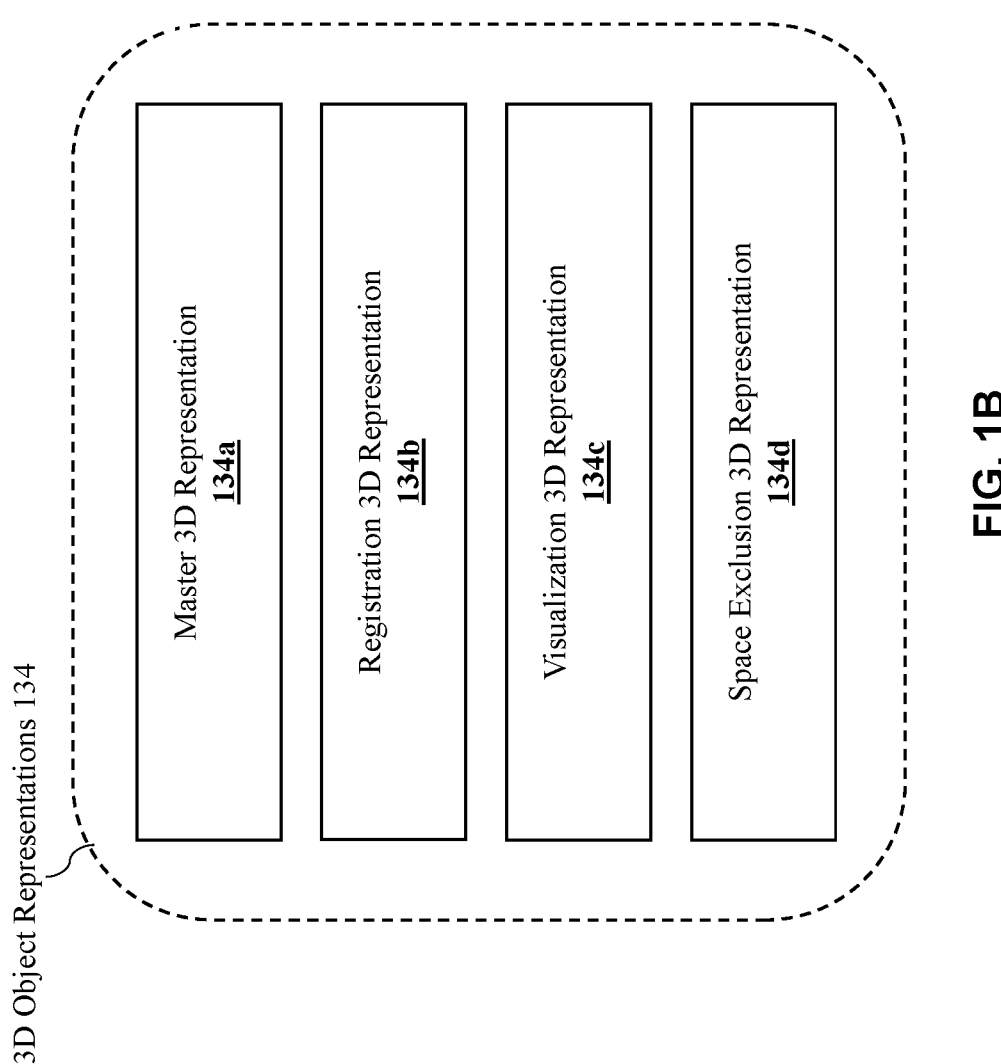
FIG. 1B illustrates example 3D object representations of the system illustrated in FIG. 1A in accordance with exemplary embodiments.
Figure 1C:
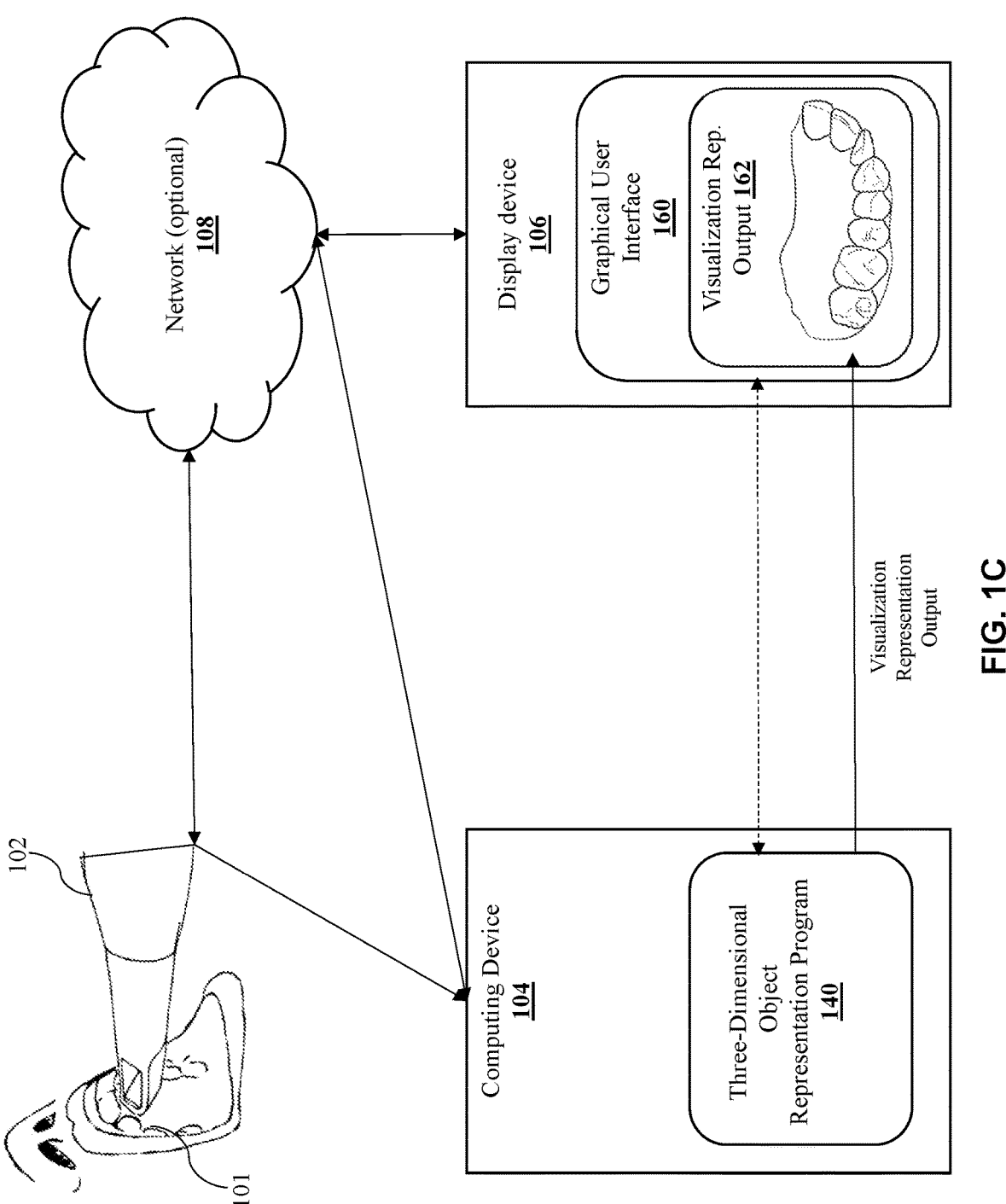

System Overview for Generating a Digital Three-Dimensional Representation of a Dental Object During Scanning with a Dental Imaging Device FIG. 1A illustrates system 100 for generating a digital three-dimensional representation of a dental object during scanning with a dental imaging device in accordance with exemplary embodiments.

The imaging device 102 may be configured to capture or generate image data 103. The imaging device may be any imaging device capable of capturing, storing, compiling, and organizing visual data, e.g., the image data 103, and receiving and sending that data to and from other computing devices, such as the computing device 104, and/or the display device 106. In an exemplary embodiment, the imaging device 102 may be a dental imaging device such as an intra-oral scanning device. For example, the imaging device 102 may be a TRIOS or Lab dental scanner by 3Shape A/S, or any other intro-oral scanner as disclosed in WO 2002/16867 "Method and Apparatus for Three-Dimensional Optical Scanning of Interior Surfaces" filed on 24 Aug. 2001, WO 2010/048960 A1 "Scanner with Feedback Control" filed on 28 Oct. 2009, WO 2010/145669 "Focus Scanning Apparatus" filed on 17 Jun. 2010, WO 2012/083967 A1 "Optical System in 3D Focus Scanner" filed on 21 Dec. 2011, WO 2012/168322 "Dual-resolution 3D Scanner" filed on 6 Jun. 2012, WO 2013/010910 "Detection of a Movable Object when 3D Scanning a Rigid Object" filed on 12 Jul. 2012, WO 2013/132091 "3D Scanner with Steam Autoclavable Tip containing a Heated Optical Element" filed on 9 Mar. 2013, WO 2014/000745 "3D Intraoral Scanner measuring Fluorescence" filed on 27 Jun. 2013, WO 2014/125037 "Focus Scanning Apparatus Recording Color" filed on 13 Feb. 2014, WO 2018/172257 "3D Scanner System with Handheld Scanner" filed on 19 Mar. 2018, WO 2020/148041 "Wireless Scanning Device" filed on 13 Dec. 2019, U.S. Pat. No. 11,076,146 "Focus Scanning Apparatus" filed on 19 Mar. 2021, which are incorporated herein by reference in their entirety.

In some embodiments, the imaging device is based on a focus scanning principle, such as depth-from-focus. In such embodiments, the imaging device comprises an optical element, such as a focus lens, which is configured to move back and forth during scanning to change the focus of the imaging device, whereby the depth can be estimated based on a focus measure. In some embodiments, the imaging device is based on a depth-from-defocus scanning principle, wherein an optical property, such as an aperture, is changed between the acquisition of two images, whereby depth can be estimated by determining the degree of defocus between the two images.

The imaging device may comprise one or more projectors configured for illuminating a surface of the dental object during scanning. The imaging device may further comprise one or more image sensors configured for acquiring sets of two-dimensional (2D) images in response to illuminating said surface. A set of 2D images may in some embodiments comprise at least two images, such as at least four images. The imaging device may be an intraoral scanner configured for generating a digital three-dimensional representation of a dental object. The imaging device may be a handheld device.

In some embodiments, the imaging device is based on triangulation, wherein at least one image sensor and a projector are positioned such that they form a triangle with respect to a point on a surface of the scanned object. As an example, a projector and an image sensor may be utilized to determine points in 3D space based on triangulation. Alternatively, the imaging device may comprise two or more image sensors viewing the scene or scanned object from two different directions, wherein the image sensors are configured to acquire a set of images, wherein a correspondence problem is solved based on triangulation. The correspondence problem generally refers to the problem of ascertaining which parts of one image correspond to which parts of another image. Specifically, the projector may be configured to project a plurality of projector rays, which are projected onto a surface of the scanned object. In particular, solving the correspondence problem may include the steps of determining image features in the images within a set of images, and further associate said image features with a specific projector ray. Subsequently, the depth of each projector ray may be computed, whereby a 3D representation of the scanned object may be generated.

The image data 103 may be any visual data such as, but not limited to, initial scan patches and/or subsequent new scan patches of an object being imaged by the imaging device 102, e.g. the object 101. In an exemplary embodiment, the imaging device 102 is a dental imaging device as discussed above and the image data 103 includes depth data of the object being scanned. For example, the image data 103 may be 2.5-dimensional image data, e.g., contain depth and color data, or three-dimensional image data of the dental object, e.g. the object 101.

The computing device 104 may include, for example, one or more processors 110, a memory 120, a storage 130, and a three-dimensional object representation program 140. The device 104 may be a desktop computer, a notebook, a laptop computer, a tablet computer, a handheld device, a smart-phone, a thin client, or any other electronic device or computing system capable of storing, compiling, and orga-nizing audio, visual, or textual data and receiving and sending that data to and from other computing devices, such as the imaging device 102, and/or the display device 240. For example, the computer system 500 illustrated in FIG. 5 and discussed in more detail below may be a suitable configuration of the computing device 104.

The one or more processors 110 may include a graphics processing unit (GPU) 112 or one or more central processing units (CPU). The processor(s) 104 may be a special purpose or general purpose processor device specifically configured to perform the functions discussed herein. The processor 110 unit or device as discussed herein may be a single processor, a plurality of processors, or combinations thereof. Processor devices may have one or more processor "cores." In an exemplary embodiment, the processor 110 is configured to perform the functions associated with the modules of the three-dimensional object representation program 140 as discussed below with reference to FIGS. 2A, 2B, 3, 4A, and 4B. The processor 110, such as the GPU 112, may be specially configured to perform the functions of the three-dimensional object representation program 140 discussed herein. For example, in exemplary embodiments, the pro-cessor 110 is configured to generate the three-dimensional object representations such as, but not limited to, the three-dimensional object representations 134. The one or more processors may form part of the system disclosed herein. In some embodiments, the processor(s) are configured for generating three-dimensional (3D) scan patches in real-time, wherein each 3D scan patch is generated based on a given set of 2D images. In some embodiments, the processor(s) are configured for generating the digital three-dimensional (3D) representation of the dental object in real-time during scan-ning, wherein the 3D representation is generated based on registration of said 3D scan patches. In general, the proces-sor(s) may be configured for carrying out the steps of the computer-implemented methods disclosed herein.

The memory 120 can be a random access memory, read-only memory, or any other known memory configura-tions. Further, the memory 120 may include one or more additional memories including the storage 130 in some embodiments. The memory 120 and the one or more addi-tional memories can be read from and/or written to in a well-known manner. In an embodiment, the memory and the one or more additional memories can be non-transitory computer readable recording media. Memory semiconduc-tors (e.g., DRAMs, etc.) can be means for providing soft-ware to the computing device such as the three-dimensional object representation program 140. Computer programs, e.g., computer control logic, can be stored in the memory 120.

The storage 130 can include, for example, image data 103, and three-dimensional object representations 134. The stor-age 130 can be deployed on one or more nodes, e.g., storage or memory nodes, or one or more processing-capable nodes such as a server computer, desktop computer, notebook computer, laptop computer, tablet computer, handheld device, smart-phone, thin client, or any other electronic device or computing system capable of storing, compiling, and/or processing data and computer instructions (e.g., image data 103, and three-dimensional object representa-tions 134), and receiving and sending that data to and from other devices, such as the imaging device 102, and/or the display device 106. The storage 130 can be any suitable storage configuration, such as, but not limited to, a relational database, a structured query language (SQL) database, a distributed database, or an object database, etc. Suitable configurations and storage types will be apparent to persons having skill in the relevant art.

The three-dimensional object representations 134 can include a digital master three-dimensional representation 134a, a digital registration three-dimensional representation 134b, a digital visualization three-dimensional representa-tion 134c, and a digital space exclusion representation 134d. A digital space exclusion three-dimensional representation is further described in WO 2013/010910 A1 filed on 12 Jul. 2012 by the same applicant, and is herein incorporated by reference in its entirety. Any of the digital three-dimensional representations, such as the digital master three-dimensional representation 134a and/or the digital visualization three-dimensional representation 134c, may be, for example, but not limited to a point cloud model, a signed distance model, a triangulated point cloud model, a collection of point clouds optionally with additional information such as uncertainty estimates or color(s), a collection of triangulated point clouds (aka scan patches), a polygon mesh, a volumetric representation such as a voxel model, a parametrized sur-face, a surface elements model, or any other suitable three-dimensional representational model. The digital master three-dimensional representation 134a may be a three-di-mensional model based on all image data 103, such as all scan patches, received from the imaging device 102. The digital registration three-dimensional representation 134b may be a three-dimensional model used to register, e.g., any new scan patches, received from the imaging device 102, which are preferably then subsequently added to one or more of the other digital three-dimensional representations 134, such as the digital master representation.

The method may comprise the step of continuously obtaining new 3D scan patches in real-time during scanning, and registering said new 3D scan patches to a digital 3D representation, such as the registration 3D representation, during scanning, whereby said scan patches form part of the digital 3D representation. In general, any of the steps of the disclosed methods herein may be performed continuously and/or in real-time during scanning of the dental object.

In some embodiments, the digital registration 3D repre-sentation is a computed representation based on the digital master representation. As an example, the registration rep-resentation may be computed based on averaging data contained in the digital master representation, e.g. to gen-erate a computed average surface, which is based on the location and/or orientation of scan patches in the digital master representation. Advantageously, new scan patches are registered to the registration representation, e.g. defining the aforementioned average surface, as opposed to registering them to the digital master representation. The digital three-dimensional visualization representation 136c may be a three-dimensional model of the object 101 that is output to the display device 106 to be viewed by a user of the three-dimensional object representation program 140. The digital space exclusion representation 134d may be a three-dimensional model used to calibrate the image data 103 received from the imaging device 102. The three-dimensional object representations 134 are discussed in more detail below with reference to FIGS. 2A, 2B, and 3. In general, a three-dimensional representation is understood herein to either constitute or comprise one or more of the following: a point cloud, a point cloud with additional attributes such as point normals or point colors, a triangulated point cloud (a triangle mesh), a polygonal mesh, a volumetric representation/voxel model, parametric representations e.g. a spline representation.

The three-dimensional object representation program 140 is a software component that utilizes the image data 103 received from the imaging device 102 and/or stored in the storage 130 to generate the three-dimensional object representations 134 and then outputs a three-dimensional visualization output 162, e.g. the three-dimensional visualization representation 134c. In an exemplary embodiment, the three-dimensional object representation program 140 includes an image data receipt module 142, a three-dimensional representation generation module 144, a three-dimensional representation update module 146, a key frame selection module 148, a re-registration module 150, a space exclusion module 152, and a display module 154. The three-dimensional object representation program 140 is a software component specifically programmed to implement the methods and functions disclosed herein for generating a digital three-dimensional representation of a dental object during scanning with a dental imaging device. The three-dimensional object representation program 140 and the modules 144-154 are discussed in more detail below with reference to FIGS. 2A, 2B, 3, 4A, and 4B.

The three-dimensional object representation program 140 can include a graphical user interface 160. The graphical user interface 160 can include components used to receive input from the imaging device 102, the computing device 104, and/or the display device 106 and transmit the input to the three-dimensional object representation program 140 or conversely to receive information from the three-dimensional object representation program 140 and display the information on the computing device 104, and/or the display device 106. In an example embodiment, the graphical user interface 160 uses a combination of technologies and devices, such as device drivers, to provide a platform to enable users of the computing device 104, and/or the display device 106 to interact with the three-dimensional object representation program 140. In the example embodiment, the graphical user interface 160 receives input from a physical input device, such as a keyboard, mouse, touchpad, touchscreen, camera, microphone, etc. In an exemplary embodiment, the graphical user interface 160 may display a three-dimensional visualization representation output 162. While the graphical user interface 160 is illustrated as part of the display device 106, it can be appreciated that the graphical user interface 160 is a part of the three-dimensional object representation program 140 and may be a part of the computing device 104, and/or the display device 106.

While the processor 110, the memory 120, the storage 130, and the three-dimensional object representation program 140 are illustrated as part of the computing device 104, it can be appreciated that each of these elements or a combination thereof can be a part of a separate computing device.

The display device 106 can include the graphical user interface 160. The display device 106 be any computing device, such as, but not limited to, a cell phone, a server computer, a desktop computer, a notebook, a laptop computer, a tablet computer, a handheld device, a smart-phone, a thin client, or any other electronic device or computing system capable of receiving display signals from another computing device, such as the imaging device 102, and/or the computing device 104, etc. and outputting those display signals to a display unit such as, but not limited to, an LCD screen, plasma screen, LED screen, DLP screen, CRT screen, e-ink screen etc. For example, the graphical user interface 160 may receive the three-dimensional visualization representation output 162 from the three-dimensional object representation program 140 and display the three-dimensional visualization representation output 162 on the display device 106. Further, the graphical user interface 160 may receive data input files, e.g., the image data 103, from a user and transmit those data input files, e.g., the image data 103, to the three-dimensional object representation program 140. The data input files e.g., the image data 103, can include a single piece of data (e.g., a single scan patch from the imaging device 102) or multiple pieces of data (e.g., a plurality of scan patches from the imaging device 102). The display device 106 may communicate with the imaging device 102, and/or the computing device 104 via a hard-wired connection or via the network 108. For example, the display device 106 may have a hard-wired connection to the image device such as, but not limited to, a USB connection, an HDMI connection, a display port connection, a Mini DisplayPort connection, a VGA connection, a DVI connection or any other known hard-wired connection capable of transmitting and/or receiving data between the imaging device 102, the computing device 104, and/or the display device 106.

While the display device 106 is illustrated as being separate from the imaging device 102, and the computing device 104, it can be appreciated that the display device 106 can be a part of the imaging device 102, and/or the computing device 104. For example, the computer system 500 illustrated in FIG. 5 and discussed in more detail below may be a suitable configuration of the imaging device 102, the computing device 104, and/or the display device 106.

The optional network 108 may be any network suitable for performing the functions as disclosed herein and may include a local area network (LAN), a wide area network (WAN), a wireless network (e.g., WiFi), a personal area network (PAN) (e.g. Bluetooth), a near-field communication (NFC) network, a mobile communication network, a satellite network, the Internet, fiber optic, coaxial cable, other hardwired networks, infrared, radio frequency (RF), or any combination of the foregoing. Other suitable network types and configurations will be apparent to persons having skill in the relevant art. In general, the network 108 can be any combination of connections and protocols that will support communications between the imaging device 102, the computing device 104, and/or the display device 106. In some embodiments, the network 108 may be optional based on the configuration of the imaging device 102, the computing device 104, and the display device 106.

Referring to FIG. 10 illustrates an example system 100 for generating a digital three-dimensional representation of a dental object during scanning with a dental imaging device. The object 101 may be any object capable of being scanned by the imaging device 102. In an exemplary embodiment, the object 101 is an oral cavity or any part of an oral cavity including, but not limited to, dentition, gingiva, retromolar trigone, hard palate, soft palate, and floor of the mouth, etc. The imaging device 102 may capture 2.5-dimensional data, e.g. the image data 103, of the object 101 and transmit that data to the computing device 104. The three-dimensional object representation program 140 receives the image data 103 from the imaging device 102 and generates and continually updates the three-dimensional object representations 132, as discussed in more detail below with reference to FIGS. 2A, 2B, and 3. The three-dimensional object representation program 140 may output the digital three-dimensional visualization representation 134c to the display device, e.g., via the graphical user interface 160, as the visualization representation output 162.

Figure 2A:
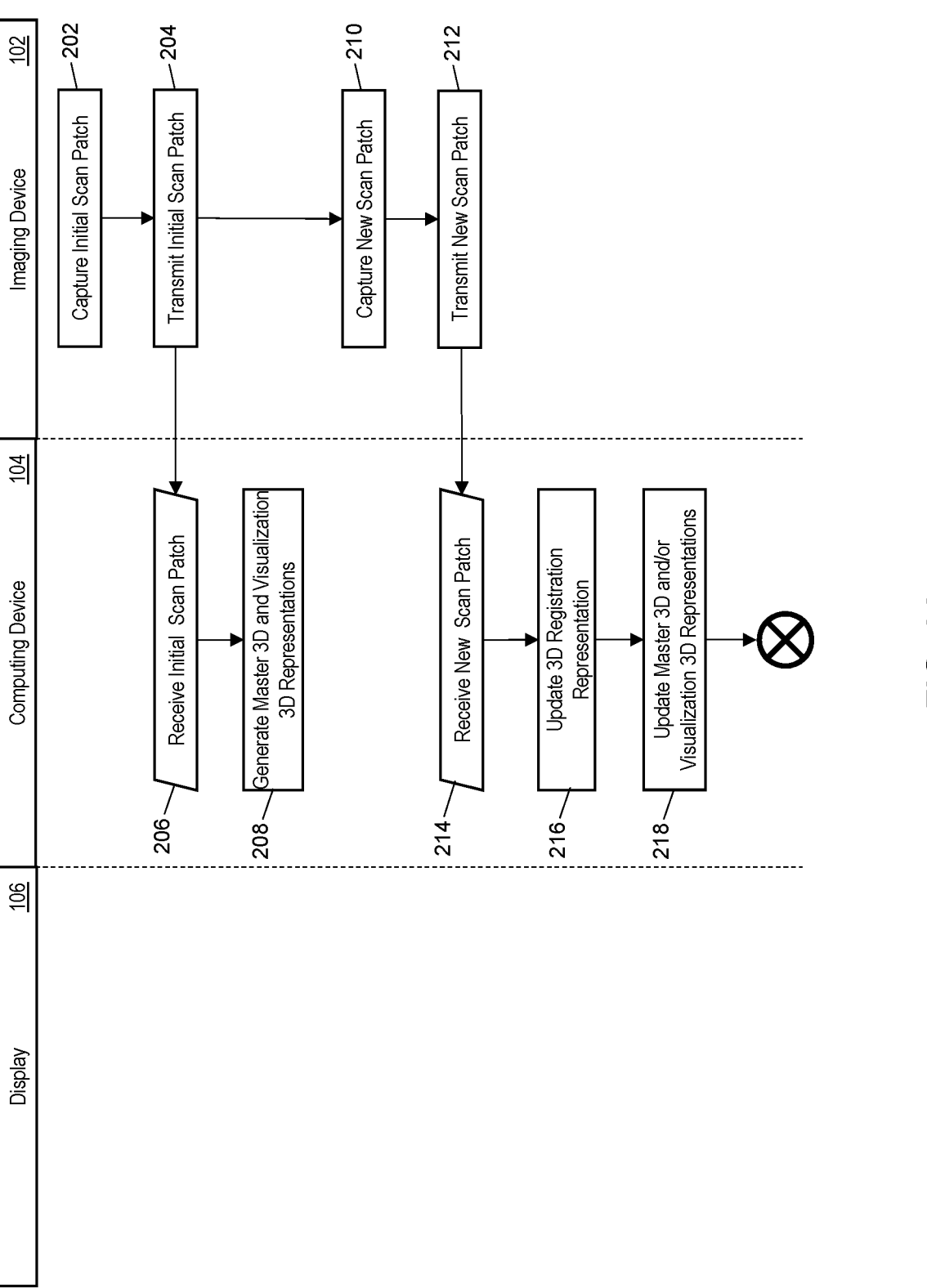
FIGS. 2A-2B is a flow chart illustrating a process for generating a digital three-dimensional representation of a dental object during scanning with a dental imaging device in accordance with exemplary embodiments.
Figure 2B:
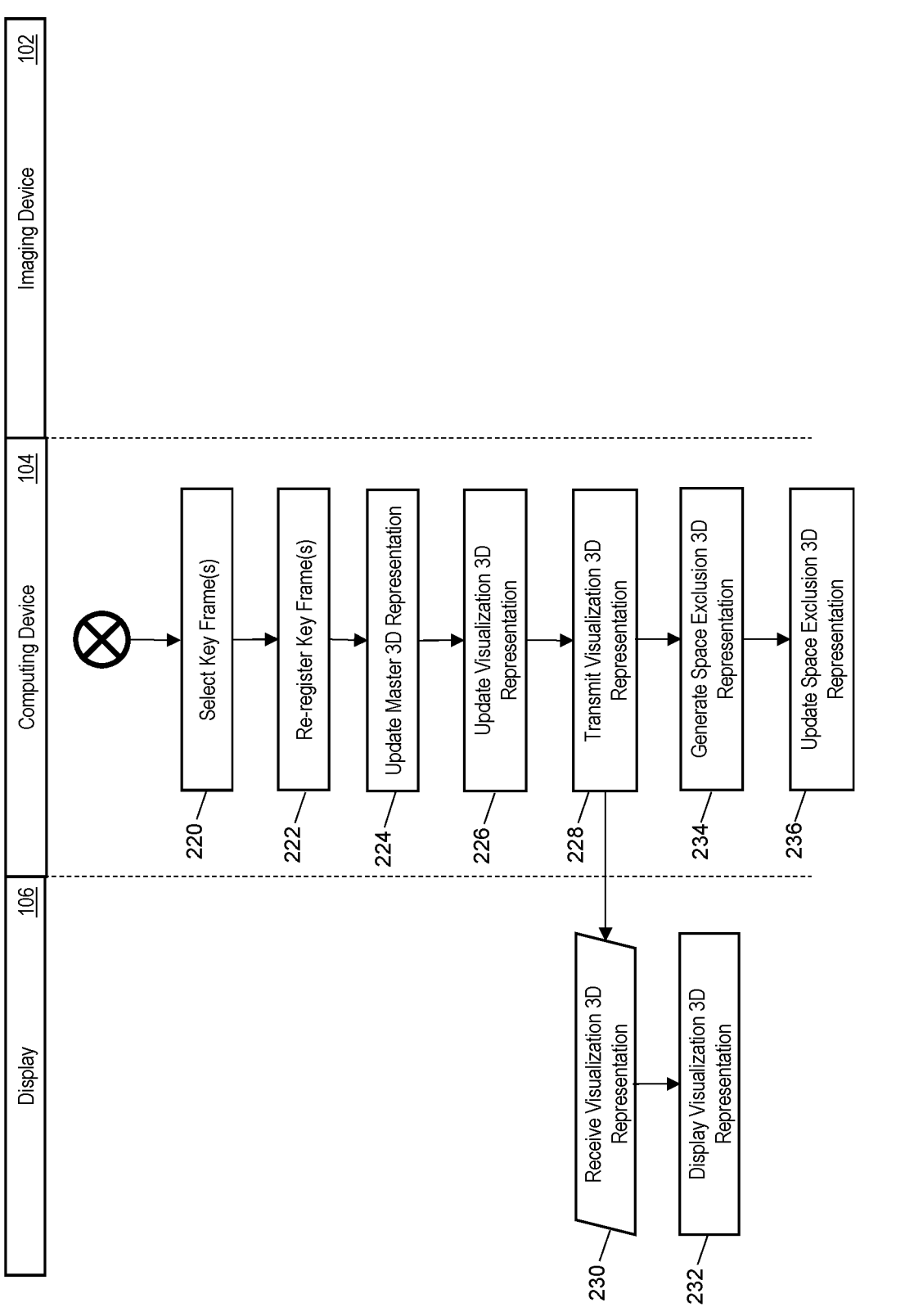

Exemplary Process for Generating a Digital Three-Dimensional Representation of a Dental Object During Scanning with a Dental Imaging Device FIGS. 2A-2B illustrates a process for generating a digital three-dimensional (3D) representation of a dental object during scanning with a dental imaging device in the system 100 of FIG. 1A. The digital 3D representation(s) may be generated in real-time during scanning.

In step 202, the imaging device 102 may capture, e.g., scan, an initial scan patch, e.g., the image data 103, of a dental object such as a patient's oral cavity, e.g. object 101, including, but not limited to, dentition, gingiva, retromolar trigone, hard palate, soft palate, and floor of the mouth, etc. The image data 103 captured by the imaging device 102 may contain a threshold amount of three-dimensional data of the dental object to constitute the initial scan patch of the dental object. Examples of three-dimensional data may include a point cloud, a collection of triangulated points, a parametrized surface, a voxel model, or other forms of representing three-dimensional data. Thus, a 3D scan patch may be understood as including or constituting any of said aforementioned examples of three-dimensional data. In step 204, the imaging device 102 may transmit the initial scan patch, e.g., the image data 103, to the computing device 104 using a suitable communication network and method, e.g., the network 108. The computing device 104 is preferably configured to determine whether the initial received scan patch should be accepted as the initial scan patch of the three-dimensional representation. This determination may be performed by assessing whether the initial scan patch contains at least the threshold amount of three-dimensional data. This threshold amount may be pre-defined by the three-dimensional object representation program 140 or by a user of the three-dimensional object representation program 140. For example, the threshold may be that the initial scan patch of the dental object must contain at least twenty-five percent valid three-dimensional data.

In step 206, the computing device 104 may receive the initial scan patch, e.g., the image data 103, from the imaging device 102. In step 208, the computing device 104 may generate a digital master three-dimensional representation, e.g., the digital master three-dimensional representation 134a, and a digital visualization three-dimensional representation, e.g., the digital visualization three-dimensional representation 134c, based on the initial scan patch, e.g., the image data 103.

In step 210, the imaging device 102 may capture, e.g., scan, new scan patch, e.g., the image data 103, of a dental object such as a patient's oral cavity, e.g. object 101, including, but not limited to, dentition, gingiva, retromolar trigone, hard palate, soft palate, and floor of the mouth, etc., where the new scan patch is received after the initial scan patch. In step 212, the imaging device 102 may transmit the new scan patch, e.g., the image data 103, to the computing device 104 using a suitable communication network and method, e.g., the network 108.

In step 214, the computing device 104 may receive the new scan patch, e.g., the image data 103, from the imaging device 102. Thus, the method may include the step of continuously obtaining new 3D scan patches in real-time during scanning. In step 216, the computing device 104 may update the digital registration three-dimensional representation 134b with the new scan patch. In an embodiment, updating the digital registration three-dimensional representation 134b with the new scan patch may include creating a temporary three-dimensional representation of the dental object from the digital master three-dimensional representation 134a based on all previously received, if available, scan patches of the dental object in the region of the new scan patch. Further, the temporary three-dimensional representation of the dental object may be an averaged surface based on the previous scan patches of the dental object. The temporary three-dimensional representation of the dental object may only exist as long as the new scan patch is being registered and then the temporary three-dimensional representation of the dental object may be discarded.

In step 218, the computing device 104 may update the digital master three-dimensional representation 134a and/or the digital visualization three-dimensional representation 134c by registering the new scan patch, e.g. the image data 103. Scan patch registration may include registering the new scan patch to one or more previously captured scan patches of the dental object, such as registering the new scan patch to the digital three-dimensional (3D) representation. Registration of a new scan patch may be understood as determining the position and/or the orientation of the new scan patch relative to another object/collection of objects (such as a collection of scan patches, e.g. a three-dimensional representation or model). Registration of scan patches may be performed using an iterative closest point (ICP) algorithm. Generally, ICP algorithms are employed to minimize the difference between two clouds of points, typically by keeping one point cloud fixed, the reference, while transforming the other to best match the reference. The registration step may further include the actual positioning of the new scan patch relative to the collection of objects/scan patches. In an exemplary embodiment the digital master three-dimensional representation 134a and the digital visualization three-dimensional representation 134c are updated with a first update frequency. This first update frequency may be faster than a second or third update frequency described below.

For example, the first update frequency may depend on how the imaging device 102 is moved about the object 101, e.g., the first update frequency may be faster the faster the imaging device 102 is moved around the object 101. The first update frequency may be correlated to or depend on any of the following measures: the frame rate of the imaging device, the amount of surface imaged by the imaging device per second, the amount of registered surface, a fixed time interval, occurrence of landmarks in the scan, or change in color (measured between consecutive scan patches).

In step 220, the computing device 104 may select one or more key frames of the scan patches of the digital master three-dimensional representation 134a. In other words, a sub-set of 3D scan patches among the obtained or registered 3D scan patches may be selected, wherein said selection is performed during scanning. Said sub-set of scan patches may also be referred to herein as key frames. There are multiple ways to select one or more key frames from a collection of scan patches. In one embodiment, the key frames are selected by selecting every n'th scan patch as a key frame, where n is a predefined number, such as selecting every $5^{th}$, $10^{th}$, or $20^{th}$ scan patch, of the received scan patches. In another embodiment, the key frames are selected uniformly in time, such that e.g. every second or every $10^{th}$ of a second, a scan patch is selected to be a key frame. In yet another embodiment, the key frames are selected such that they are uniformly distributed in 3D space in the digital master three-dimensional representation. In this embodiment, the key frames may furthermore be selected such that their orientation is taken into account, i.e. such that they are distributed uniformly in relation to both position and orientation in 3D space. Another alternative is to select key frames based on global descriptors for the scan patches (similar to a hashing of the geometry) and select the scan patches that cover the model in descriptor space. In yet another embodiment, the key frames are selected based on the texture images in the scan patches. In yet another embodiment, selecting the one or more key frames may include the computing device 104 identifying a portion of overlap between a new scan patch and previously identified key frames, where the portion of overlap is a pre-determined distance between each key frame of the one or more key frames. The predetermined distance (either in time or space) between the key frames may be determined based on, for example, but not limited to, center of mass of the scan patches, a timestamp of the scan patches (e.g., a time when the scan patch was received from the imaging device 102), a color of the scan patches, a texture of the scan patches, and a shape of the scan patches, etc. For example, the computing device may identify a center of mass of each scan patch, e.g., the image data 103, where each of the selected one or more key frames has a center of mass a pre-determined distance away from each other, the pre-determined distance being a distance between a center of mass of each of the one or more key frames. It can be appreciated that the key frames may be selected in any way and based on any criteria such that each key frame is sufficiently different from any other key frame, e.g., depicts an area of the dental object sufficiently different from any other key frame.

Figure 7:
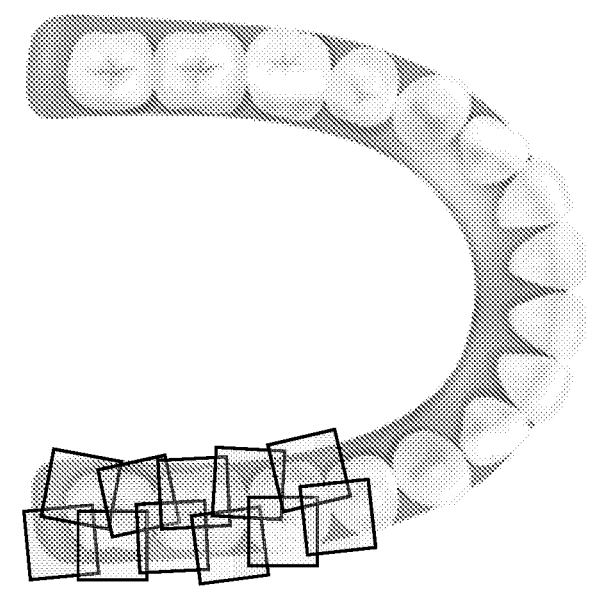
FIG. 7 is a schematic illustration of an exemplary three-dimensional representation of a dental object, specifically the lower jaw of a patient. The figure further illustrates some overlapping key frames, said key frames constituting a sub-set of all the obtained and/or registered scan patches.

Key frames may also be referred to herein as a sub-set of 3D scan patches, such as a sub-set selected among the obtained or registered 3D scan patches. Thus, the presently disclosed method may comprise the step of selecting a sub-set of 3D scan patches among the obtained or registered 3D scan patches, wherein said selection is performed during scanning. In some embodiments, a list of 3D scan patches may be continuously generated or expanded, wherein 3D scan patches may be added to the list during scanning, said list constituting the sub-set of 3D scan patches or key frames. FIG. 7 schematically illustrates a sub-set of 3D scan patches, wherein scan patches within the sub-set overlaps. The size of each scan patch may correspond with the field of view of the imaging device. Preferably, the key frames or scan patches in the sub-set are selected such that they cover the entirety of the scanned object. As an example. the digital 3D representation, such as the digital master representation, of the dental object may contain in excess of 1000 scan patches, whereas the sub-set of 3D scan patches may contain 100 scan patches or fewer. In FIG. 7, only key frames are shown for illustrative purposes.

In step 222, the computing device 104 may re-register the one or more key frames or re-registering one or more 3D scan patches forming part of the digital 3D representation, wherein said re-registering is based on applying one or more transformations to the key frames/selected sub-set of scan patches. Re-registration may be understood as repositioning and/or reorienting one or more scan patches or key frames relative to a reference frame, such as relative to an initial scan patch or relative to a collection of scan patches. The re-registration step is preferably performed during scanning, e.g. during acquisition of image data or scan data using the imaging device. In some embodiments, the step of re-registering one or more 3D scan patches is completed before a new 3D scan patch is obtained. In some embodiments, the imaging device is configured to generate at least 20 scan patches per second, such that the method disclosed herein may include the step of obtaining at least 20 new 3D scan patches per second. In some embodiments, the re-registration step is completed within a time frame of less than 1 second, such as less than 200 milliseconds. Re-registration of the scan patches or key frames may include manipulating the one or more key frames such as, but not limited to, rotating, and/or translating the one or more key frames. Manipulating the one or more key frames may also be understood herein as applying one or more transformations, such as geometric transformations, to the key frames. Non-key frames, i.e. scan patches not forming part of the sub-set, may inherit the applied transformations based on one or more criteria, such as the vicinity to key frames. Thus, the step of re-registering may comprise translating and/or rotating one or more previously registered 3D scan patches relative to each other or relative to the three-dimensional (3D) representation. In step 224, the computing device 104 may update the digital master three-dimensional representation 134a based on the re-registration of the one or more key frames. This step (224) preferably includes the step of re-registering a plurality of scan patches, such as all scan patches, that are part of the digital 3D representation, e.g. the digital master 3D representation, wherein said re-registration is based on the re-registration of the key frames. During the re-registration of the scan patches that are not key frames, said scan patches may inherit any manipulations or transformations performed to the key frames/sub-set.

In some embodiments, scan patches that are not part of the sub-set (i.e. not key frames) are transformed according to a weighted average of the transformations applied to one or more neighboring key frames, wherein neighboring frames may be selected according to a predefined distance criteria. In some embodiments, all scan patches forming part of the digital 3D representation are simultaneously re-registered, or considered for re-registration, in the re-registration step. In an embodiment, the update of the digital master three-dimensional representation 134a is done at a second update frequency. The second update frequency may be variable or fixed. For example, the second update frequency may depend upon how fast the imaging device 102 moves to a new surface or area of the object 101. Alternatively, the second update frequency may be fixed, e.g., update based on a set number of scan patches received from the imaging device 102. The variable and fixed regimes may also be combined, such that there is at least a lower limit on the second update frequency, which may then be increased depending on the movement/speed of the imaging device 102. The second update frequency may additionally or alternatively depend on any of the following metrics: a variance between surface in the scan patches, user input (e.g. from button(s) or from a display), or geometrical features on the scanned object 101. As an example, when scanning a flat surface the second update frequency may be higher than when scanning a highly curved surface or the other way around. Therefore, it can be appreciated that the first and second update frequencies of the digital master model representation 134*a* can be the same or asynchronous.

In step 226, the computing device 104 may update the digital visualization three-dimensional representation 134*c* based on the re-registration of the one or more key frames. Updating a three-dimensional representation, such as updating the digital visualization three-dimensional representation, may be understood as any one or more of the following actions: transforming/warping/distorting at least a part of the representation, replacing data in at least a part of the representation, replacing all data of the representation with new data, adding data to the representation, or averaging existing data in the representation with new data. The digital visualization three-dimensional representation 134*c* may be updated based on the re-registration of the one or more key frames with a third update frequency. In an exemplary embodiment, the third update frequency is an aggregate update frequency of one or more voxel update frequencies associated with each voxel or sub-volume of the digital visualization three-dimensional representation 134*c*. Each of the one or more voxel update frequencies may have a different voxel update multiplier based on how many of the one or more scan patches overlap each voxel of the digital visualization three-dimensional representation 134*c*. In an embodiment, the third update frequency may be based on how many scan patches of the dental object, e.g., the object 101, are received from the imaging device 102 within a specific region of the dental object, e.g., the object 101. For example, if a specific region is being imaged by the imaging device 102, that specific region may have more scan patches than any other region of the object 101, which may indicate that that specific region is the region currently being viewed by a user of the three-dimensional object representation program 140. In an embodiment, updating the digital visualization three-dimensional representation 134*c* with the third update frequency may include determining a portion of the digital visualization three-dimensional representation 134*c* that has not been updated for a pre-determined period of time and updating the portion of the digital visualization three-dimensional representation 134*c* that has not been updated for the pre-determined period of time. For example, determining the portion of the digital visualization three-dimensional representation 134*c* that has not been updated for a pre-determined period of time may include the computing device 104 identifying a number of scan patches corresponding to each portion of the dental object, e.g., the object 101, received since a previous scan patch corresponding to the same portion of the dental object, e.g., the object 101, was received from the imaging device 102. In an embodiment, updating the digital visualization three-dimensional representation 134*c* with the third update frequency may depend on the position and/or movement of the imaging device with respect to the representation 134*c*. As an example, areas/parts of the object 101 that are in the field of view of the imaging device 102 may be updated before other portions of the digital visualization three-dimensional representation.

In step 228, the computing device 104 may transmit the digital visualization three-dimensional representation 134*c*, e.g., as the visualization representation output 162, to the display device 106 using any suitable communication network and method, e.g., the network 108. In step 230, the display device 106 may receive the digital visualization three-dimensional representation 134*c*, e.g., as the visualization representation output 162. In step 232, the display device 106 may display the digital visualization three-dimensional representation 134*c*, e.g., as the visualization representation output 162. For example, the display device 106 may display the digital visualization three-dimensional representation 134*c* to a user of the imagine device 102, the computing device 104, and/or the display devoice 106 via the graphical user interface 160.

In step 234, the computing device 104 may generate a digital space exclusion three-dimensional representation 134*d* based on the scan patches, i.e. the image data 103, received from the imaging device 102 and/or stored in the storage 130. In step 236, the computing device 104 may update the digital space exclusion three-dimensional representation 134*d* based on the re-registration of the one or more key frames. Space exclusion is performed by creating a depth map for each scan patch, e.g., the image data 103, and projecting one scan patch into the depth map of another scan patch to exclude parts in the first scan patch that are behind the surface in the second patch. The projection is done using the scanner, e.g., the imaging device 102, calibration and the relative position of the two scan patches. Since the relative position of the two scan patches changes after re-registration, the space exclusion result also changes. Therefore, space exclusion is also re-computed after re-registration, similar to how the rendering model is rebuilt after re-registration. Space exclusion is discussed in detail in WO 2013/010910 "Detection of a Movable Object when 3D Scanning a Rigid Surface" filed on 12 Jul. 2012, which is herein incorporated by reference in its entirety.

Exemplary Method for Generating a Digital Three-Dimensional Representation of a Dental Object During Scanning with a Dental Imaging Device FIG. 3 illustrates a method 300 for generating a digital three-dimensional representation of a dental object during scanning with a dental imaging device in accordance with exemplary embodiments.

The method 300 can include block 302 of storing, e.g., by the computing device 104, a digital master three-dimensional representation 134*a* of the dental object, e.g. the object 101. The digital master three-dimensional representation 134*a* of the dental object may be generated using one or more scan patches of the dental object captured via the imaging device 102, where each of the scan patches are associated with a portion of the dental object. For example, the dental object may be a dental patient's oral cavity and the scan patches may be associated with portions of the dental patient's oral cavity such as, but not limited to, dentition, gingiva, retromolar trigone, hard palate, soft palate, and floor of the mouth, etc. In an exemplary embodiment, the digital master three-dimensional representation 134*a* may be stored in the storage 130 of the computing device 104.

The method 300 can include block 304 of storing, e.g., by the computing device 104, a digital registration three-dimensional representation 134*b* of the dental object, e.g., the object 101. The digital registration three-dimensional representation 134*b* may be generated using the one or more scan patches of the dental object captured via the imaging device 102. For example, the digital registration three-dimensional representation 134*b* may be a three-dimensional representation of a dental patient's oral cavity generated from scan patches of the dental patient's oral cavity including, but not limited to, dentition, gingiva, retromolar trigone, hard palate, soft palate, and floor of the mouth, etc. In an exemplary embodiment, the digital registration three-dimensional representation 134*b* may be stored in the storage 130 of the computing device 104.

The method 300 can include block 306 of storing, e.g., by the computing device 104, a digital visualization three-dimensional representation 134*c* of the dental object, e.g., the object 101. For example, the digital visualization three-dimensional representation 134c may be a three-dimensional representation of a dental patient's oral cavity generated from scan patches of the dental patient's oral cavity including, but not limited to, dentition, gingiva, retromolar trigone, hard palate, soft palate, and floor of the mouth, etc. The digital visualization three dimensional representation 134c may be output to a display, e.g., the display device 106. In an exemplary embodiment, the digital visualization three-dimensional representation 134c may be stored in the storage 130 of the computing device 104.

The method 300 can include block 308 of receiving, e.g., by the computing device 104, a new scan patch, e.g., the image data 103, of the dental object, e.g., the object 101, from the imaging device 102. For example, the computing device 104 may receive a new scan patch of a portion of a dental patient's oral cavity. In an exemplary embodiment, the image data receipt module 142 of the three-dimensional representation program 140 can be configured to execute the method of block 308.

The method 300 can include block 310 of updating, e.g., by the computing device 104, the digital registration three-dimensional representation 134b with the new scan patch. For example, the digital registration three-dimensional representation 134b may be updated with a new scan patch of a portion of a dental patient's oral cavity. In an embodiment, updating the digital registration three-dimensional representation 134b with the new scan patch may include creating a temporary three-dimensional representation of the dental object from the digital master three-dimensional representation 134a based on all previously received, if available, scan patches of the dental object in the region of the new scan patch. Further, the temporary three-dimensional representation of the dental object may be an averaged surface based on the previous scan patches of the dental object. The temporary three-dimensional representation of the dental object may only exist as long as the new scan patch is being registered and then the temporary three-dimensional representation of the dental object may be discarded. In an exemplary embodiment, the three-dimensional update module 146 of the three-dimensional representation program 140 can be configured to execute the method of block 310.

The method 300 can include block 312 of updating, e.g., by the computing device 104, the digital master three-dimensional representation 134a and the digital visualization three-dimensional representation 134c with a first update frequency by registering the new scan patch. The registration of the new scan patch may include registering the new scan patch to the one or more previously captured scan patches. For example, a new scan patch of a portion of a dental patient's oral cavity may be registered to previously captured scan patches of the dental patient's oral cavity. In an exemplary embodiment the digital master three-dimensional representation 134a and the digital visualization three-dimensional representation 134c are updated with a first update frequency. This first update frequency may be faster than a second or third update frequency described above and below. For example, the first update frequency may depend on how the imaging device 102 is moved about the object 101, e.g., the first update frequency will be faster the faster the imaging device 102 is moved around the object 101. In an exemplary embodiment, the three-dimensional update module 146 of the three-dimensional representation program 140 can be configured to execute the method of block 312.

The method 300 can include block 314 of selecting, e.g., by the computing device 104, one or more key frames of the scan patches of the digital master three-dimensional representation 134a. In an embodiment, selecting the one or more key frames may include the computing device 104 identifying a portion of overlap between the one or more key frames, where the portion of overlap is a pre-determined distance between each key frame of the one or more key frames. For example, the key frames may be chosen from scan patches of a dental patient's oral cavity and the overlap may be overlap between scan patches depicting the same teeth of the patient's oral cavity. The predetermined distance between the key frames may be determined based on, for example, but not limited to, center of mass of the scan patches, a timestamp of the scan patches (e.g., a time when the scan patch was received from the imaging device 102), a color of the scan patches, a texture of the scan patches, and a shape of the scan patches, etc. For example, the computing device may identify a center of mass of each scan patch, e.g., the image data 103, where each of the selected one or more key frames has a center of mass a pre-determined distance away from each other, the pre-determined distance being a distance between a center of mass of each of the one or more key frames. It can be appreciated that the key frames may be selected in any way and based on any criteria such that each key frame is sufficiently different from any other key frame, e.g., depicts an area of the dental object sufficiently different from any other key frame. In an exemplary embodiment, the key frame selection module 148 of the three-dimensional representation program 140 can be configured to execute the method of block 314.

The method 300 can include block 316 of re-registering, e.g., by the computing device 104, the one or more key frames. Re-registration of the key frames can include manipulating the one or more key frames, such as by, but not limited to, rotating, and/or translating the one or more key frames. For example, the key frames chosen from scan patches of a dental patient's oral cavity may be manipulated such that the key frames are correctly aligned with one another and accurately depict the patient's oral cavity. In an exemplary embodiment, the re-registration module 150 of the three-dimensional representation program 140 can be configured to execute the method of block 316.

The method 300 can include block 318 of updating, e.g., by the computing device 104, the digital master three-dimensional representation 134a based on the re-registration of the one or more key frames with a second update frequency. The second update frequency may be variable or fixed. For example, the second update frequency may depend upon how fast the imaging device 102 moves to a new surface or area of the object 101, e.g., a new section or area of the patient's oral cavity. Alternatively, the second update frequency may be fixed, e.g., update based on a set number of scan patches received from the imaging device 102. Therefore, it can be appreciated that the first and second update frequencies of the digital master model representation 134a can be the same or asynchronous. In an exemplary embodiment, the three-dimensional update module 146 of the three-dimensional representation program 140 can be configured to execute the method of block 318.

The method 300 can include block 320 of updating, e.g., by the computing device 104, the digital visualization three-dimensional representation 134c based on the re-registration of the one or more key frames with a third update frequency. In an exemplary embodiment, the third update frequency is an aggregate update frequency of one or more voxel update frequencies associated with each voxel or sub-volume of the digital visualization three-dimensional representation 134c. Each of the one or more voxel update frequencies may have a different voxel update multiplier based on how many of the one or more scan patches overlap each voxel of the digital visualization three-dimensional representation 134c. In an embodiment, the third update frequency may be based on how many scan patches of the dental object, e.g., the object 101, are received from the imaging device 102 within a specific region of the dental object, e.g., the object 101. For example, if a specific region, e.g. a dental patient's lower right oral cavity, is being imaged by the imaging device 102, that specific region may have more scan patches than any other region of the object 101, which may indicate that that specific region is the region currently being viewed by a user of the three-dimensional object representation program 140. In an embodiment, updating the digital visualization three-dimensional representation 134c with the third update frequency may include determining a portion of the digital visualization three-dimensional representation 134c that has not been updated for a pre-determined period of time and updating the portion of the digital visualization three-dimensional representation 134c that has not been updated for the pre-determined period of time. For example, determining the portion of the digital visualization three-dimensional representation 134c that has not been updated for a pre-determined period of time may include the computing device 104 identifying a number of scan patches corresponding to each portion of the dental object, e.g., the object 101, received since a previous scan patch corresponding to the same portion of the dental object, e.g., the object 101, was received from the imaging device 102. In an exemplary embodiment, the three-dimensional update module 146 of the three-dimensional representation program 140 can be configured to execute the method of block 320.

Figure 4A:
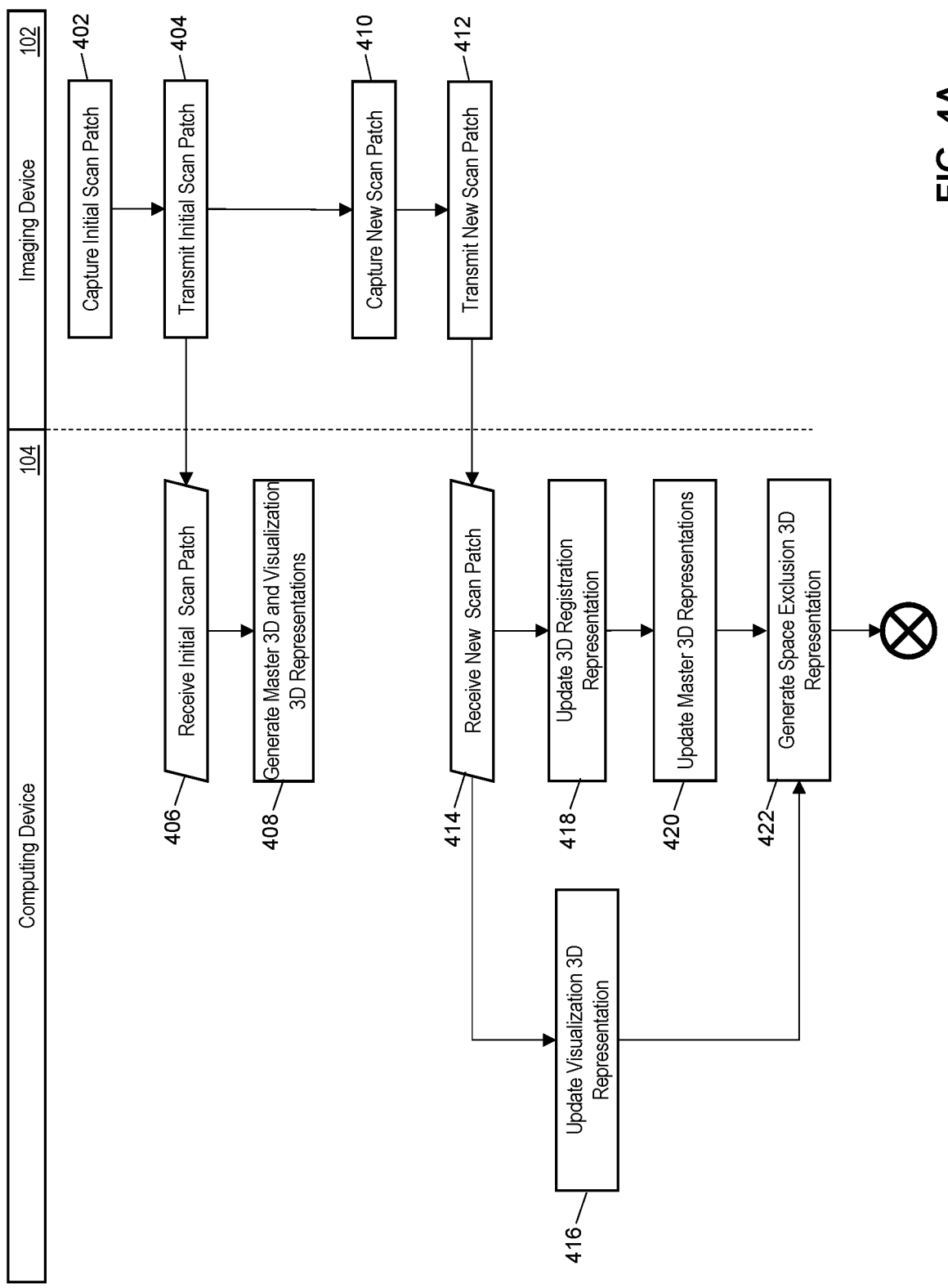
FIGS. 4A-4B is a flow chart illustrating a process for generating a digital three-dimensional representation of a dental object during scanning with a dental imaging device in accordance with exemplary embodiments.
Figure 4B:
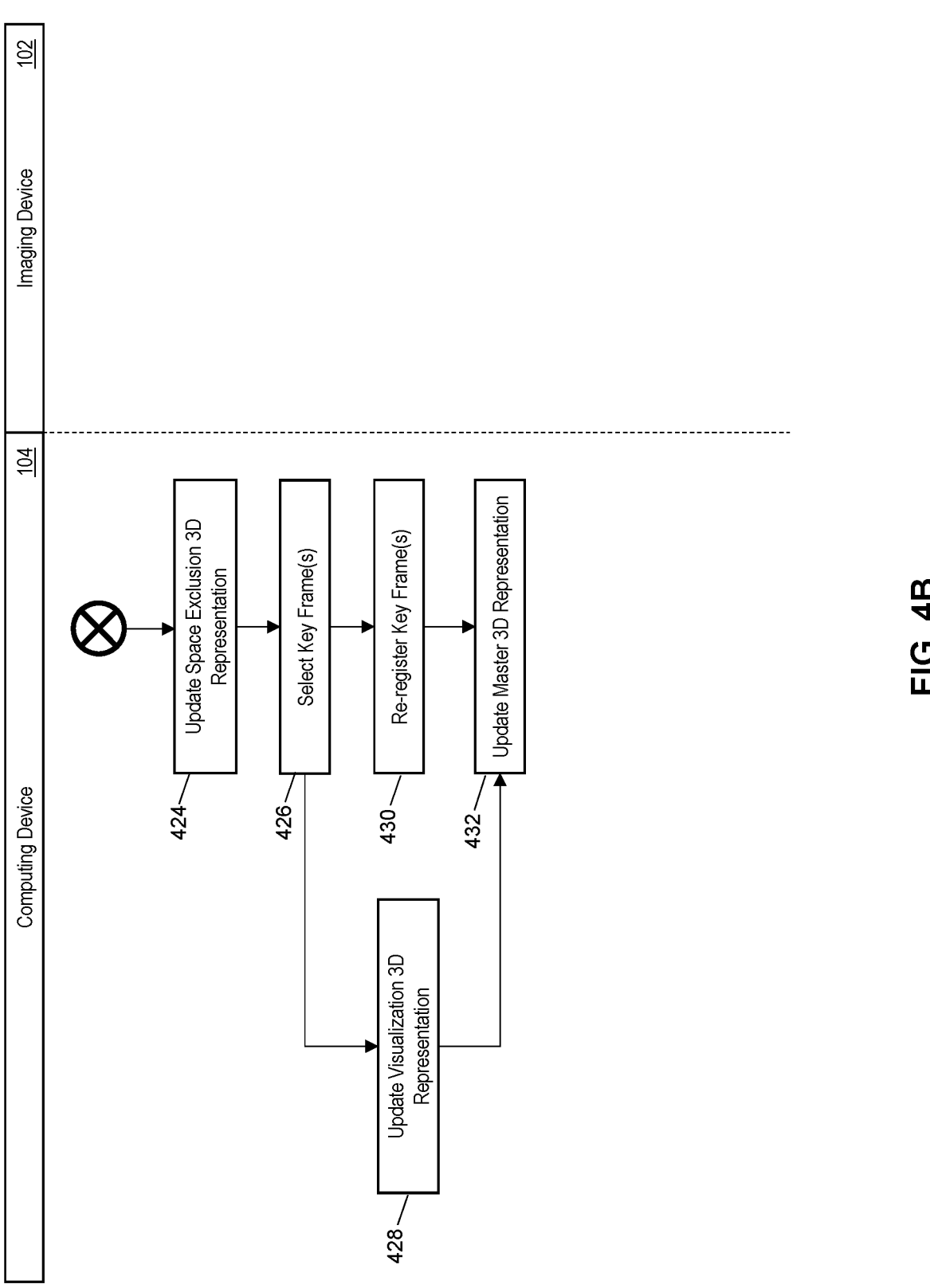

Exemplary Process for Generating a Digital Three-Dimensional Representation of a Dental Object During Scanning with a Dental Imaging Device FIGS. 4A-4B illustrates a process for generating a digital three-dimensional representation of a dental object during scanning with a dental imaging device in the system 100 of FIG. 1A.

In step 402, the imaging device 102 may capture, e.g., scan, an initial scan patch, e.g., the image data 103, of a dental object such as a patient's oral cavity, e.g. object 101, including, but not limited to, dentition, gingiva, retromolar trigone, hard palate, soft palate, and floor of the mouth, etc. The image data 103 captured by the imaging device 102 may contain a threshold amount of three-dimensional data of the dental object to constitute the initial scan patch of the dental object. Examples of three-dimensional data may include a point cloud, a collection of triangulated points, a parametrized surface, a voxel model, or other forms of representing three-dimensional data. In step 404, the imaging device 102 may transmit the initial scan patch, e.g., the image data 103, to the computing device 104 using a suitable communication network and method, e.g., the network 108. The computing device 104 is preferably configured to determine whether the initial received scan patch should be accepted as the initial scan patch of the three-dimensional representation. This determination may be performed by assessing whether the initial scan patch contains at least the threshold amount of three-dimensional data. This threshold amount may be pre-defined by the three-dimensional object representation program 140 or by a user of the three-dimensional object representation program 140. For example, the threshold may be that the initial scan patch of the dental object must contain at least twenty-five percent valid three-dimensional data.

In step 406, the computing device 104 may receive the initial scan patch, e.g., the image data 103, from the imaging device 102. In step 408, the computing device 104 may generate a digital master three-dimensional representation, e.g., the digital master three-dimensional representation 134a, and a digital visualization three-dimensional representation, e.g., the digital visualization three-dimensional representation 134c, based on the initial scan patch, e.g., the image data 103.

In step 410, the imaging device 102 may capture, e.g., scan, new scan patch, e.g., the image data 103, of a dental object such as a patient's oral cavity, e.g. object 101, including, but not limited to, dentition, gingiva, retromolar trigone, hard palate, soft palate, and floor of the mouth, etc., where the new scan patch is received after the initial scan patch. In step 412, the imaging device 102 may transmit the new scan patch, e.g., the image data 103, to the computing device 104 using a suitable communication network and method, e.g., the network 108.

In step 414, the computing device 104 may receive the new scan patch, e.g., the image data 103, from the imaging device 102. From step 414, the process 400 may perform steps 418-422 concurrently with step 416.

In step 416, the computing device 104 may update the digital visualization three-dimensional representation 134c based on the new scan patch. Updating a three-dimensional representation, such as updating the digital visualization three-dimensional representation, may be understood as any one or more of the following actions: transforming/warping/distorting at least a part of the representation, replacing data in at least a part of the representation, replacing all data of the representation with new data, adding data to the representation, or averaging existing data in the representation with new data. The digital visualization three-dimensional representation 134c may be updated based on the new scan patch with a third update frequency. In an exemplary embodiment, the third update frequency is an aggregate update frequency of one or more voxel update frequencies associated with each voxel or sub-volume of the digital visualization three-dimensional representation 134c. Each of the one or more voxel update frequencies may have a different voxel update multiplier based on how many of the one or more scan patches overlap each voxel of the digital visualization three-dimensional representation 134c. In an embodiment, the third update frequency may be based on how many scan patches of the dental object, e.g., the object 101, are received from the imaging device 102 within a specific region of the dental object, e.g., the object 101. For example, if a specific region is being imaged by the imaging device 102, that specific region may have more scan patches than any other region of the object 101, which may indicate that that specific region is the region currently being viewed by a user of the three-dimensional object representation program 140. In an embodiment, updating the digital visualization three-dimensional representation 134c with the third update frequency may include determining a portion of the digital visualization three-dimensional representation 134c that has not been updated for a pre-determined period of time and updating the portion of the digital visualization three-dimensional representation 134c that has not been updated for the pre-determined period of time. For example, determining the portion of the digital visualization three-dimensional representation 134c that has not been updated for a pre-determined period of time may include the computing device 104 identifying a number of scan patches corresponding to each portion of the dental object, e.g., the object 101, received since a previous scan patch corresponding to the same portion of the dental object, e.g., the object 101, was received from the imaging device 102. In an embodiment, updating the digital visualization three-dimensional representation 134c with the third update frequency may depend on the position and/or movement of the imaging device with respect to the representation 134c. As an example, areas/parts of the object 101 that are in the field of view of the imaging device 102 may be updated before other portions of the digital visualization three-dimensional representation.

In step 418, the computing device 104 may update the digital registration three-dimensional representation 134b with the new scan patch. In an embodiment, updating the digital registration three-dimensional representation 134b with the new scan patch may include creating a temporary three-dimensional representation of the dental object from the digital master three-dimensional representation 134a based on all previously received, if available, scan patches of the dental object in the region of the new scan patch. Further, the temporary three-dimensional representation of the dental object may be an averaged surface based on the previous scan patches of the dental object. The temporary three-dimensional representation of the dental object may only exist as long as the new scan patch is being registered and then the temporary three-dimensional representation of the dental object may be discarded.

In step 420, the computing device 104 may update the digital three-dimensional representation, e.g. the digital master three-dimensional representation 134a, by registering the new scan patch, e.g. the image data 103. Scan patch registration may include registering the new scan patch to one or more previously captured scan patches of the dental object. Registration of a new scan patch may be understood as determining the position and/or the orientation of the new scan patch relative to another object/collection of objects (such as a collection of scan patches). The registration step may further include the actual positioning of the new scan patch relative to the collection of objects/scan patches. A collection of scan patches stitched together may constitute the digital three-dimensional (3D) model. In an exemplary embodiment the digital master three-dimensional representation 134a is updated with a first update frequency. This first update frequency may be faster than a second or third update frequency described below. For example, the first update frequency may depend on how the imaging device 102 is moved about the object 101, e.g., the first update frequency may be faster the faster the imaging device 102 is moved around the object 101. The first update frequency may be correlated to or depend on any of the following measures: the frame rate of the imaging device, the amount of surface imaged by the imaging device per second, the amount of registered surface, a fixed time interval, occurrence of landmarks in the scan, or change in color (measured between consecutive scan patches).

In step 422, the computing device 104 may generate a digital space exclusion three-dimensional representation 134d based on the scan patches, i.e. the image data 103, received from the imaging device 102 and/or stored in the storage 130. In step 424, the computing device 104 may update the digital space exclusion three-dimensional representation 134d based on the new scan patch, e.g., the image data 103. Space exclusion is performed by creating a depth map for each scan patch, e.g., the image data 103, and projecting one scan patch into the depth map of another scan patch to exclude parts in the first scan patch that are behind the surface in the second patch. The projection may be done using the scanner, e.g., the imaging device 102, calibration and the relative position of the two scan patches. Since the relative position of the two scan patches changes after re-registration, the space exclusion result also changes. Therefore, space exclusion is preferably also re-computed after re-registration, similar to how the rendering model is rebuilt after re-registration. Space exclusion is discussed in detail in WO 2013/010910 "Detection of a Movable Object when 3D Scanning a Rigid Surface" filed on 12 Jul. 2012, which is herein incorporated by reference in its entirety.

In step 426, the computing device 104 may select one or more key frames of the scan patches of the digital master three-dimensional representation 134a. In other words, a sub-set of 3D scan patches among the obtained or registered 3D scan patches may be selected, wherein said selection is performed during scanning. Said sub-set of scan patches may also be referred to herein as key frames. There are multiple ways to select one or more key frames from a collection of scan patches. In one embodiment, the key frames are selected by selecting every n'th scan patch as a key frame, where n is a predefined number, such as selecting every $5^{th}$, $10^{th}$, or $20^{th}$ scan patch, of the received scan patches. In another embodiment, the key frames are selected uniformly in time, such that e.g. every second or every $10^{th}$ of a second, a scan patch is selected to be a key frame. In yet another embodiment, the key frames are selected such that they are uniformly distributed in 3D space in the digital master three-dimensional representation. In this embodiment, the key frames may furthermore be selected such that their orientation is taken into account, i.e. such that they are distributed uniformly in relation to both position and orientation in 3D space. Another alternative is to select key frames based on global descriptors for the scan patches (similar to a hashing of the geometry) and select the scan patches that cover the model in descriptor space. In yet another embodiment, the key frames are selected based on the texture images in the scan patches. In yet another embodiment, selecting the one or more key frames may include the computing device 104 identifying a portion of overlap between a new scan patch and previously identified key frames, where the portion of overlap is a pre-determined distance between each key frame of the one or more key frames. The predetermined distance (either in time or space) between the key frames may be determined based on, for example, but not limited to, center of mass of the scan patches, a timestamp of the scan patches (e.g., a time when the scan patch was received from the imaging device 102), a color of the scan patches, a texture of the scan patches, and a shape of the scan patches, etc. For example, the computing device may identify a center of mass of each scan patch, e.g., the image data 103, where each of the selected one or more key frames has a center of mass a pre-determined distance away from each other, the pre-determined distance being a distance between a center of mass of each of the one or more key frames. It can be appreciated that the key frames may be selected in any way and based on any criteria such that each key frame is sufficiently different from any other key frame, e.g., depicts an area of the dental object sufficiently different from any other key frame. From step 426, the process 400 may perform steps 430-432 concurrently with step 428.

In step 428, the computing device 104 may update the digital visualization three-dimensional representation 134c based on the selected one or more key frames. Updating a three-dimensional representation, such as updating the digital visualization three-dimensional representation, should be understood as any one or more of the following actions: transforming/warping/distorting at least a part of the representation, replacing data in at least a part of the representation, replacing all data of the representation with new data, adding data to the representation, or averaging existing data in the representation with new data. The digital visualization three-dimensional representation 134c may be updated based on the selected one or more key frames with a third update frequency. In an exemplary embodiment, the third update frequency is an aggregate update frequency of one or more voxel update frequencies associated with each voxel or sub-volume of the digital visualization three-dimensional representation 134c. Each of the one or more voxel update frequencies may have a different voxel update multiplier based on how many of the one or more scan patches overlap each voxel of the digital visualization three-dimensional representation 134c. In an embodiment, the third update frequency may be based on how many scan patches of the dental object, e.g., the object 101, are received from the imaging device 102 within a specific region of the dental object, e.g., the object 101. For example, if a specific region is being imaged by the imaging device 102, that specific region may have more scan patches than any other region of the object 101, which may indicate that that specific region is the region currently being viewed by a user of the three-dimensional object representation program 140. In an embodiment, updating the digital visualization three-dimensional representation 134c with the third update frequency may include determining a portion of the digital visualization three-dimensional representation 134c that has not been updated for a pre-determined period of time and updating the portion of the digital visualization three-dimensional representation 134c that has not been updated for the pre-determined period of time. For example, determining the portion of the digital visualization three-dimensional representation 134c that has not been updated for a pre-determined period of time may include the computing device 104 identifying a number of scan patches corresponding to each portion of the dental object, e.g., the object 101, received since a previous scan patch corresponding to the same portion of the dental object, e.g., the object 101, was received from the imaging device 102. In an embodiment, updating the digital visualization three-dimensional representation 134c with the third update frequency may depend on the position and/or movement of the imaging device with respect to the representation 134c. As an example, areas/parts of the object 101 that are in the field of view of the imaging device 102 may be updated before other portions of the digital visualization three-dimensional representation.

In step 430, the computing device 104 may re-register the one or more key frames. Re-registration may be understood as repositioning and/or reorienting one or more scan patches or key frames relative to a reference frame, such as relative to an initial scan patch or relative to a collection of scan patches. Re-registration of the key frames may include manipulating the one or more key frames such as, but not limited to, rotating, and/or translating the one or more key frames. In step 432, the computing device 104 may update the digital master three-dimensional representation 134a based on the re-registration of the one or more key frames. This step (432) preferably includes the step of re-registering a plurality of scan patches, such as all scan patches, that are part of the digital master 3D representation, wherein said re-registration is based on the re-registration of the key frames. During the re-registration of the scan patches that are not key frames, said scan patches may inherit any manipulations or transformations performed to the key frames. In an embodiment, the update of the digital master three-dimensional representation 134a is done at a second update frequency. The second update frequency may be variable or fixed. For example, the second update frequency may depend upon how fast the imaging device 102 moves to a new surface or area of the object 101. Alternatively, the second update frequency may be fixed, e.g., update based on a set number of scan patches received from the imaging device 102. The variable and fixed regimes may also be combined, such that there is at least a lower limit on the second update frequency, which may then be increased depending on the movement/speed of the imaging device 102. The second update frequency may additionally or alternatively depend on any of the following metrics: a variance between surface in the scan patches, user input (e.g. from button(s) or from a display), or geometrical features on the scanned object 101. As an example, when scanning a flat surface the second update frequency may be higher than when scanning a highly curved surface or the other way around. Therefore, it can be appreciated that the first and second update frequencies of the digital master model representation 134a can be the same or asynchronous.

The process 400 may proceed from step 432 to steps 228-230 of the process 200.

Computer System Architecture

Figure 5:
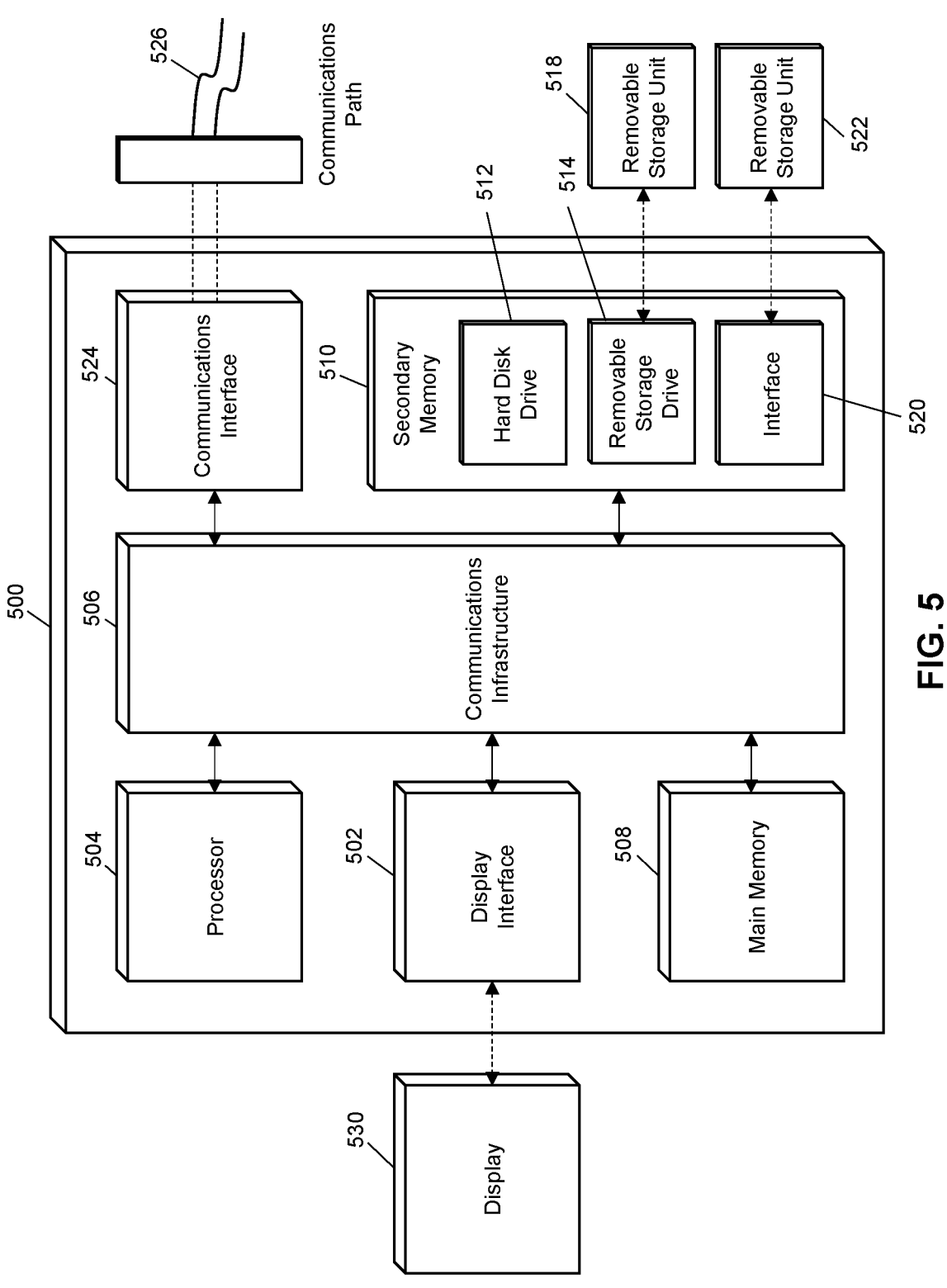
FIG. 5 is a block diagram illustrating a computer system architecture in accordance with exemplary embodiments.

FIG. 5 illustrates a computer system 500 in which embodiments of the present disclosure, or portions thereof, may be implemented as computer-readable code. For example, the imaging device 102, the computing device 104, and/or the display device 106 of FIG. 1A may be implemented in the computer system 500 using hardware, software, firmware, non-transitory computer readable media having instructions stored thereon, or a combination thereof and may be implemented in one or more computer systems or other processing systems. Hardware, software, or any combination thereof may embody modules and components used to implement the methods of FIGS. 1A-4B If programmable logic is used, such logic may execute on a commercially available processing platform configured by executable software code to become a specific purpose computer or a special purpose device (e.g., programmable logic array, application-specific integrated circuit, etc.). A person having ordinary skill in the art may appreciate that embodiments of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device. For instance, at least one processor device and a memory may be used to implement the above described embodiments.

A processor unit or device as discussed herein may be a single processor, a plurality of processors, or combinations thereof. Processor devices may have one or more processor "cores." The terms "computer program medium," "non-transitory computer readable medium," and "computer usable medium" as discussed herein are used to generally refer to tangible media such as a removable storage unit 518, a removable storage unit 522, and a hard disk installed in hard disk drive 512.

Various embodiments of the present disclosure are described in terms of this example computer system 500. After reading this description, it will become apparent to a person skilled in the relevant art how to implement the present disclosure using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 504 may be a special purpose or a general purpose processor device specifically configured to perform the functions discussed herein. The processor device 504 may be connected to a communications infrastructure 506, such as a bus, message queue, network, multi-core message-passing scheme, etc. The network may be any network suitable for performing the functions as disclosed herein and may include a local area network (LAN), a wide area network (WAN), a wireless network (e.g., WiFi), a mobile communication network, a satellite network, the Internet, fiber optic, coaxial cable, infrared, radio frequency (RF), or any combination thereof. Other suitable network types and configurations will be apparent to persons having skill in the relevant art. The computer system 500 may also include a main memory 508 (e.g., random access memory, read-only memory, etc.), and may also include a secondary memory 410. The secondary memory 510 may include the hard disk drive 512 and a removable storage drive 514, such as a floppy disk drive, a magnetic tape drive, an optical disk drive, a flash memory, etc.

The removable storage drive 514 may read from and/or write to the removable storage unit 518 in a well-known manner. The removable storage unit 518 may include a removable storage media that may be read by and written to by the removable storage drive 514. For example, if the removable storage drive 514 is a floppy disk drive or universal serial bus port, the removable storage unit 518 may be a floppy disk or portable flash drive, respectively. In one embodiment, the removable storage unit 518 may be non-transitory computer readable recording media.

In some embodiments, the secondary memory 510 may include alternative means for allowing computer programs or other instructions to be loaded into the computer system 500, for example, the removable storage unit 522 and an interface 520. Examples of such means may include a program cartridge and cartridge interface (e.g., as found in video game systems), a removable memory chip (e.g., EEPROM, PROM, etc.) and associated socket, and other removable storage units 522 and interfaces 520 as will be apparent to persons having skill in the relevant art.

Data stored in the computer system 500 (e.g., in the main memory 508 and/or the secondary memory 510) may be stored on any type of suitable computer readable media, such as optical storage (e.g., a compact disc, digital versatile disc, Blu-ray disc, etc.) or magnetic tape storage (e.g., a hard disk drive). The data may be configured in any type of suitable database configuration, such as a relational database, a structured query language (SQL) database, a distributed database, an object database, etc. Suitable configurations and storage types will be apparent to persons having skill in the relevant art.

The computer system 500 may also include a communications interface 524. The communications interface 524 may be configured to allow software and data to be transferred between the computer system 500 and external devices. Exemplary communications interfaces 524 may include a modem, a network interface (e.g., an Ethernet card), a communications port, a PCMCIA slot and card, etc. Software and data transferred via the communications interface 524 may be in the form of signals, which may be electronic, electromagnetic, optical, or other signals as will be apparent to persons having skill in the relevant art. The signals may travel via a communications path 526, which may be configured to carry the signals and may be implemented using wire, cable, fiber optics, a phone line, a cellular phone link, a radio frequency link, etc.

The computer system 500 may further include a display interface 502. The display interface 502 may be configured to allow data to be transferred between the computer system 500 and external display 530. Exemplary display interfaces 502 may include high-definition multimedia interface (HDMI), digital visual interface (DVI), video graphics array (VGA), etc. The display 530 may be any suitable type of display for displaying data transmitted via the display interface 502 of the computer system 500, for example a cathode ray tube (CRT) display, liquid crystal display (LCD), light-emitting diode (LED) display, capacitive touch display, thin-film transistor (TFT) display, etc.

Computer program medium and computer usable medium may refer to memories, such as the main memory 508 and secondary memory 510, which may be memory semiconductors (e.g., DRAMs, etc.). These computer program products may be means for providing software to the computer system 500. Computer programs (e.g., computer control logic) may be stored in the main memory 508 and/or the secondary memory 510. Computer programs may also be received via the communications interface 524. Such computer programs, when executed, may enable computer system 500 to implement the present methods as discussed herein. In particular, the computer programs, when executed, may enable processor device 504 to implement the processes and methods illustrated by FIGS. 2A, 2B, 3, 4A, and 4B as discussed herein. Accordingly, such computer programs may represent controllers of the computer system 500. Where the present disclosure is implemented using software, the software may be stored in a computer program product and loaded into the computer system 500 using the removable storage drive 514, interface 520, and hard disk drive 512, or communications interface 524.

The processor device 504 may comprise one or more modules or engines configured to perform the functions of the computer system 500. Each of the modules or engines may be implemented using hardware and, in some instances, may also utilize software, such as corresponding to program code and/or programs stored in the main memory 508 or secondary memory 510. In such instances, program code may be compiled by the processor device 504 (e.g., by a compiling module or engine) prior to execution by the hardware of the computer system 500. For example, the program code may be source code written in a programming language that is translated into a lower level language, such as assembly language or machine code, for execution by the processor device 504 and/or any additional hardware components of the computer system 500. The process of compiling may include the use of lexical analysis, preprocessing, parsing, semantic analysis, syntax-directed translation, code generation, code optimization, and any other techniques that may be suitable for translation of program code into a lower level language suitable for controlling the computer system 500 to perform the functions disclosed herein. It will be apparent to persons having skill in the relevant art that such processes result in the computer system 500 being a specially configured computer system 500 uniquely programmed to perform the functions discussed above.

Exemplary Method for Generating a Digital Three-Dimensional Representation of a Dental Object During Scanning with a Dental Imaging Device FIG. 6 illustrates a method 600 for generating a digital three-dimensional representation of a dental object during scanning with a dental imaging device in accordance with exemplary embodiments.

The method 600 can include block 602 of generating a digital three-dimensional (3D) representation of the dental object based on registration and stitching of a plurality of 3D scan patches. In an exemplary embodiment, the digital three-dimensional representation may be stored in the storage 130 of the computing device 104.

The method 600 can include block 604 of obtaining new 3D scan patches in real-time during scanning. In an exemplary embodiment, the new 3D scan patches are obtained using the imaging device 102. In some cases, the imaging device 102 is configured to provide image data, e.g. in the form of 2.5-dimensional data, which may be understood as images from which depth can be inferred, such that 3-dimensional data can be generated based on said 2.5-dimensional data. In some cases, the 3-dimensional data are point clouds. The 3-dimensional data may be generated by a computing device external to the imaging device.

The method 600 can include block 606 of registering said new 3D scan patches to the digital 3D representation during scanning, whereby said scan patches form part of the digital 3D representation. In an exemplary embodiment, new 3D scan patches are registered to a digital registration 3D representation. As an example, said registration 3D representation may be a computed representation based on the digital master 3D representation, e.g. based on averaging data in the digital master 3D representation.

The method 600 can include block 608 of selecting a sub-set of 3D scan patches among the obtained or registered 3D scan patches, wherein said selection is performed during scanning. In an exemplary embodiment, the sub-set of 3D scan patches at least partially overlaps each other as shown in FIG. 7. The sub-set of 3D scan patches may further be selected such that they sufficiently cover the scanned object.

The method 600 can include block 610 of re-registering one or more 3D scan patches forming part of the digital 3D representation, wherein said re-registering is based on applying one or more transformations to the selected sub-set of scan patches. In an exemplary embodiment, said transformations include any of translation and/or rotation. As an example, a plurality or all 3D scan patches of the digital 3D representation, e.g. the digital master representation, may be re-registered based on how the selected sub-set are transformed. In some embodiments, scan patches not forming part of the selected sub-set are transformed according to a weighted average of the transformations applied to nearby scan patches within the sub-set.

Techniques consistent with the present disclosure provide, among other features, systems and methods for generating a digital three-dimensional representation of a dental object during scanning with a dental imaging device. While various exemplary embodiments of the disclosed system and method have been described above it should be understood that they have been presented for purposes of example only, not limitations. It is not exhaustive and does not limit the disclosure to the precise form disclosed. Modifications and variations are possible in light of the above teachings or may be acquired from practicing of the disclosure, without departing from the breadth or scope. Although operations can be described as a sequential process, some of the operations can in fact be performed in parallel, concurrently, and/or in a distributed environment, and with program code stored locally or remotely for access by single or multi-processor machines. In addition, in some embodiments the order of operations can be rearranged without departing from the spirit of the disclosed subject matter. It will be appreciated by those skilled in the art that the present disclosure can be embodied in other specific forms without departing from the spirit or essential characteristics thereof. The presently disclosed embodiments are therefore considered in all respects to be illustrative and not restrictive. The scope of the disclosure is indicated by the appended claims rather than the foregoing description, and all changes that come within the meaning, range, and equivalence thereof are intended to be embraced therein.

FURTHER DETAILS OF THE INVENTION

1. A computer-implemented method for generating a digital three-dimensional representation of a dental object during scanning with a dental imaging device, the method comprising:

storing a digital master three-dimensional representation of the dental object, the digital master three-dimensional representation of the dental object generated using one or more scan patches of the dental object captured via the dental imaging device, each of the scan patches being associated with a portion of the dental object;

storing a digital registration three-dimensional representation of the dental object, the digital registration three-dimensional representation generated using the one or more scan patches of the dental object captured via the dental imaging device;

storing a digital visualization three-dimensional representation of the dental object, the visualization three-dimensional representation being output to a display;

receiving a new scan patch of the dental object from the dental imaging device;

updating the digital registration three-dimensional representation with the new scan patch;

updating the digital master three-dimensional representation and the digital visualization three-dimensional representation with a first update frequency by registering the new scan patch, wherein registration comprises registering the new scan patch to the one or more previously captured scan patches;

selecting one or more key frames of the scan patches of the digital master three-dimensional representation;

re-registering the one or more key frames, wherein re-registration comprises manipulating the one or more key frames, wherein manipulating includes one or more of: rotating, and/or translating;

updating the digital master three-dimensional representation based on the re-registration of the one or more key frames, wherein the digital master three-dimensional representation is updated with a second update frequency; and updating the digital visualization three-dimensional representation based on the re-registration of the one or more key frames, wherein the digital visualization three-dimensional representation is updated with a third update frequency.

2. The method of item 1, wherein the third update frequency is an aggregate update frequency of one or more update frequencies associated with parts of the digital visualization three-dimensional representation, each of the one or more parts of the digital visualization three-dimensional representation having a different update multiplier based on how many of the one or more scan patches overlap each part of the digital visualization three-dimensional representation.

3. The method of any of the preceding items, wherein the third update frequency is an aggregate update frequency of one or more voxel update frequencies associated with each voxel of the digital visualization three-dimensional representation, each of the one or more voxel update frequencies having a different voxel update multiplier based on how many of the one or more scan patches overlap each voxel of the digital visualization three-dimensional representation.

4. The method of any of the preceding items, comprising:
receiving an initial scan patch of the dental object from the dental imaging device, the initial scan patch containing at least a threshold amount of three-dimensional data;
and generating the digital master three-dimensional representation and the digital visualization three-dimensional representation based on the initial scan patch.

5. The method of any of the preceding items, wherein the selecting of the one or more key frames for the scan patches of the digital master three-dimensional representation for re-registration comprises:
identifying a portion of overlap between the one or more key frames, the portion of overlap being a pre-determined distance between each key frame of the one or more key frames.

6. The method of any of the preceding items, wherein the selecting of the one or more key frames for the scan patches of the digital master three-dimensional representation for re-registration comprises:
identifying a center of mass of each scan patch, wherein each of the selected one or more key frames has a center of mass a pre-determined distance away from each other wherein the pre-determined distance is a distance between a center of mass of each of the one or more key frames.

7. The method of any of the preceding items, wherein the third update frequency is based on how many scan patches of the dental object are received from the dental imaging device within a specific region of the dental object.

8. The method of any of the preceding items, wherein the updating the digital visualization three-dimensional representation with the third update frequency comprises:
determining a portion of the digital visualization three-dimensional representation that has not been updated for a pre-determined period of time; and
updating the portion of the digital visualization three-dimensional representation that has not been updated for the pre-determined period of time.

9. The method of item 8, wherein the determining a portion of the digital visualization three-dimensional representation that has not been updated for the pre-determined period of time comprises:
identifying a number of scan patches corresponding to each portion of the dental object received since a previous scan patch corresponding to the same portion of the dental object was received.

10. The method of any of the preceding items, comprising:
generating a digital space exclusion three-dimensional representation based on the scan patches; and updating the digital space exclusion three-dimensional representation based on the re-registration of the one or more key frames.

11. The method of any of the preceding items, wherein the master and the digital visualization three-dimensional representations are one of a point cloud model, a signed distance model, a triangulated point cloud model, or a surface elements model.

12. The method of any of the preceding items, wherein the dental object is a patient's oral cavity and the one or more scan patches are portions of the patient's oral cavity including at least one of: dentition, gingiva, retromolar trigone, hard palate, soft palate, and floor of the mouth.

13. A system for generating a digital three-dimensional representation of a dental object during scanning with a dental imaging device, the system comprising:
a memory of a processing device configured to:
store a digital master three-dimensional representation of the dental object, the digital master three-dimensional representation of the dental object generated using one or more scan patches of the dental object captured via the dental imaging device, each of the scan patches being associated with a portion of the dental object;
store a digital registration three-dimensional representation of the dental object, the digital registration three-dimensional representation generated using the one or more scan patches of the dental object captured via the dental imaging device;
store a digital visualization three-dimensional representation of the dental object, the visualization three-dimensional representation being output to a display;
a processor of the processing device configured to:
receive a new scan patch of the dental object from the dental imaging device;
update the digital registration three-dimensional representation with the new scan patch;
update the digital master three-dimensional representation and the digital visualization three-dimensional representation with a first update frequency by registering the new scan patch, wherein registration comprises registering the new scan patch to the one or more previously captured scan patches;
select one or more key frames of the scan patches of the digital master three-dimensional representation;
re-register the one or more key frames, wherein re-registration comprises manipulating the one or more key frames, wherein manipulating includes one or more of: rotating, and/or translating;
update the digital master three-dimensional representation based on the re-registration of the one or more key frames, wherein the digital master three-dimensional representation is updated with a second update frequency; and
update the digital visualization three-dimensional representation based on the re-registration of the one or more key frames, wherein the digital visualization three-dimensional representation is updated with a third update frequency.

14. The system of item 13, wherein the third update frequency is an aggregate update frequency of one or more update frequencies associated with parts of the digital visualization three-dimensional representation, each of the one or more parts of the digital visualization three-dimensional representation having a different update multiplier based on how many of the one or more scan patches overlap each part of the digital visualization three-dimensional representation.

15. The system according to any of the items 13-14, comprising:

the processor of the processing device configured to:

receive an initial scan patch of the dental object from the dental imaging device, the initial scan patch containing at least a threshold amount of three-dimensional data; and generate the digital master three-dimensional representation and the digital visualization three-dimensional representation based on the initial scan patch.

16. The system according to any of the items 13-15, wherein the selecting of the one or more key frames for the scan patches of the digital master three-dimensional representation for re-registration comprises:

identifying a portion of overlap between the one or more key frames, the portion of overlap being a pre-determined distance between each key frame of the one or more key frames.

17. The system according to any of the items 13-16, wherein the selecting of the one or more key frames for the scan patches of the digital master three-dimensional representation for re-registration comprises:

identifying a center of mass of each scan patch, wherein each of the selected one or more key frames has a center of mass a pre-determined distance away from each other wherein the pre-determined distance is a distance between a center of mass of each of the one or more key frames.

18. The method according to any of the items 13-17, wherein the third update frequency is based on how many scan patches of the dental object are received from the dental imaging device within a specific region of the dental object.

19. The system according to any of the items 13-18, wherein the updating the digital visualization three-dimensional representation with the third update frequency comprises:

determining a portion of the digital visualization three-dimensional representation that has not been updated for a pre-determined period of time; and updating the portion of the digital visualization three-dimensional representation that has not been updated for the pre-determined period of time.

20. The system according to any of the items 13-20, wherein the determining a portion of the digital visualization three-dimensional representation that has not been updated for the pre-determined period of time comprises:

identifying a number of scan patches corresponding to each portion of the dental object received since a previous scan patch corresponding to the same portion of the dental object was received.

21. The system according to any of the items 13-20, comprising:

the processor of the processing device configured to:

generate a digital space exclusion three-dimensional representation based on the scan patches; and update the digital space exclusion three-dimensional representation based on the re-registration of the one or more key frames.

22. The system according to any of the items 13-21, wherein the master and the digital visualization three-dimensional representations are one of a point cloud model, a signed distance model, a triangulated point cloud model, or a surface elements model.

23. The system according to any of the items 13-22, wherein the dental object is a patient's oral cavity and the one or more scan patches are portions of the patient's oral cavity including at least one of: dentition, gingiva, retromolar trigone, hard palate, soft palate, and floor of the mouth.

24. The system according to any of the items 13-23, wherein the system is configured to perform the method according to any of the items 1-12.

25. A computer program product comprising instructions which, when the program is executed by a computer, cause the computer to carry out the steps of the method according to any of the items 1-12.

26. A computer-readable storage medium comprising instructions which, when executed by a computer, cause the computer to carry out the steps of the method according to any of the items 1-12.

27. A computer program product for generating a digital three-dimensional representation of a dental object during scanning with a dental imaging device, the computer program product comprising:

a computer-readable storage medium having program instructions embodied therewith, the program instructions executable by a computer to cause the computer to perform a method, comprising:

storing a digital master three-dimensional representation of the dental object, the digital master three-dimensional representation of the dental object generated using one or more scan patches of the dental object captured via the dental imaging device, each of the scan patches being associated with a portion of the dental object;

storing a digital registration three-dimensional representation of the dental object, the digital registration three-dimensional representation generated using the one or more scan patches of the dental object captured via the dental imaging device;

storing a digital visualization three-dimensional representation of the dental object, the visualization three-dimensional representation being output to a display;

receiving a new scan patch of the dental object from the dental imaging device;

updating the digital registration three-dimensional representation with the new scan patch;

updating the digital master three-dimensional representation and the digital visualization three-dimensional representation with a first update frequency by registering the new scan patch, wherein registration comprises registering the new scan patch to the one or more previously captured scan patches;

selecting one or more key frames of the scan patches of the digital master three-dimensional representation;

re-registering the one or more key frames, wherein re-registration comprises manipulating the one or more key frames, wherein manipulating includes one or more of: rotating, and/or translating;

updating the digital master three-dimensional representation based on the re-registration of the one or more key frames, wherein the digital master three-dimensional representation is updated with a second update frequency; and updating the digital visualization three-dimensional representation based on the re-registration of the one or more key frames, wherein the digital visualization three-dimensional representation is updated with a third update frequency.

28. The computer program product of item 27, wherein the third update frequency is an aggregate update frequency of one or more voxel update frequencies associated with each voxel of the digital visualization three-dimensional representation, each of the one or more voxel update frequencies having a different voxel update multiplier based on how many of the one or more scan patches overlap each voxel of the digital visualization three-dimensional representation.

29. The computer program product according to any of the items 27-28, comprising:

receiving an initial scan patch of the dental object from the dental imaging device, the initial scan patch containing at least a threshold amount of three-dimensional data; and generating the digital master three-dimensional representation and the digital visualization three-dimensional representation based on the initial scan patch.

30. The computer program product according to any of the items 27-29, wherein the selecting of the one or more key frames for the scan patches of the digital master three-dimensional representation for re-registration comprises;

identifying a portion of overlap between the one or more key frames, the portion of overlap being a pre-determined distance between each key frame of the one or more key frames.

31. The computer program product according to any of the items 27-30, wherein the selecting of the one or more key frames for the scan patches of the digital master three-dimensional representation for re-registration comprises;

identifying a center of mass of each scan patch, wherein each of the selected one or more key frames has a center of mass a pre-determined distance away from each other wherein the pre-determined distance is a distance between a center of mass of each of the one or more key frames.

32. The computer program product according to any of the items 27-31, wherein the third update frequency is based on how many scan patches of the dental object are received from the dental imaging device within a specific region of the dental object.

33. The computer program product according to any of the items 27-32, wherein the updating the digital visualization three-dimensional representation with the third update frequency comprises:

determining a portion of the digital visualization three-dimensional representation that has not been updated for a pre-determined period of time; and updating the portion of the digital visualization three-dimensional representation that has not been updated for the pre-determined period of time.

34. The computer program product of item 33, wherein the determining a portion of the digital visualization three-dimensional representation that has not been updated for the pre-determined period of time comprises:

identifying a number of scan patches corresponding to each portion of the dental object received since a previous scan patch corresponding to the same portion of the dental object was received.

35. The computer program product according to any of the items 27-34, comprising:

generating a digital space exclusion three-dimensional representation based on the scan patches; and updating the digital space exclusion three-dimensional representation based on the re-registration of the one or more key frames.

36. The computer program product according to any of the items 27-35, wherein the master and the digital visualization three-dimensional representations are one of a point cloud model, a signed distance model, a triangulated point cloud model, or a surface elements model.

37. The computer program product according to any of the items 27-36, wherein the dental object is a patient's oral cavity and the one or more scan patches are portions of the patient's oral cavity including at least one of: dentition, gingiva, retromolar trigone, hard palate, soft palate, and floor of the mouth.

38. A computer-implemented method for improving the accuracy of a digital three-dimensional representation of a dental object during scanning, the method comprising the steps of:

generating a digital three-dimensional (3D) representation of the dental object based on registration and stitching of a plurality of 3D scan patches;

continuously obtaining new 3D scan patches in real-time during scanning;

registering said new 3D scan patches to the digital 3D representation during scanning, whereby said scan patches form part of the digital 3D representation;

selecting a sub-set of 3D scan patches among the obtained or registered 3D scan patches, wherein said selection is performed during scanning; and re-registering one or more 3D scan patches forming part of the digital 3D representation, wherein said re-registering is based on applying one or more transformations to the selected sub-set of scan patches, whereby the accuracy of a digital 3D representation is improved.

39. The method of item 38, wherein the step of re-registering is performed during scanning.

40. The method of any of the items 38-39, wherein the step of re-registering comprises translating and/or rotating the one or more 3D scan patches relative to each other or relative to the three-dimensional (3D) representation.

41. The method of any of the items 38-40, wherein the step of re-registering one or more 3D scan patches is completed before a new 3D scan patch is obtained.

42. The method of any of the items 38-41, wherein the step of re-registering is completed in less than 1 second.

43. The method of any of the items 38-42, wherein the step of re-registering is completed in less than 200 milliseconds.

44. The method of any of the items 38-43, wherein at least 20 new 3D scan patches are obtained per second.

45. The method of any of the items 38-44, wherein all steps of the method are performed continuously and in real-time.

46. The method of any of the items 38-45, wherein a plurality of 3D scan patches forming part of the digital 3D representation are re-registered during the step of re-registering.

47. The method of any of the items 38-46, wherein all 3D scan patches forming part of the digital 3D representation are re-registered during the step of re-registering.

48. The method of any of the items 38-47, wherein one or more one or more transformations are applied to each 3D scan patch within the sub-set of 3D scan patches, wherein said transformation(s) include translation and/or rotation.

49. The method of any of the items 38-48, wherein 3D scan patches not forming part of the selected sub-set are transformed according to a weighted average of the transformations applied to one or more scan patches within the sub-set of 3D scan patches.

50. The method of any of the items 38-49, wherein registration of the 3D scan patches is performed using an iterative closest point algorithm.

51. The method of any of the items 38-50, wherein the re-registration of the 3D scan patches is a global registration.

52. The method of any of the items 38-51, wherein the step of re-registering comprises simultaneously applying one or more transformations to a plurality of 3D scan patches, said transformations including translation and/or rotation.

53. A data processing apparatus comprising one or more processors configured to perform the steps of the method according to any of the items 38-52.

54. A computer system comprising one or more processors configured to perform the steps of the method according to any of the items 38-52.

55. A computer program product comprising instructions which, when the program is executed by a computer, cause the computer to carry out the steps of the method according to any of the items 38-52.

56. A computer-readable data carrier having stored thereon the computer program product of item 55.

57. A computer-readable storage medium comprising instructions which, when executed by a computer, cause the computer to carry out the steps of the method according to any of the items 38-52.

58. A system for generating a digital three-dimensional representation of a dental object during scanning, the system comprising:
   a dental imaging device comprising:
      one or more projectors configured for illuminating a surface of the dental object during scanning;
      one or more image sensors configured for acquiring sets of two-dimensional (2D) images in response to illuminating said surface;
   one or more processors configured to perform the steps of the method according to any of the items 38-52.

59. The system according to item 58, wherein the dental imaging device comprises one or more processors configured to continuously generate 3D scan patches based on the acquired sets of 2D images.

The invention claimed is:

1. A computer-implemented method for improving the accuracy of a digital three-dimensional representation of a dental object during scanning, the method comprising the steps of:
   generating a digital three-dimensional (3D) representation of the dental object based on registration and stitching of a plurality of 3D scan patches;
   continuously obtaining new 3D scan patches in real-time during scanning;
   registering said new 3D scan patches to the digital 3D representation during scanning, whereby said scan patches form part of the digital 3D representation;
   selecting a sub-set of 3D scan patches among the obtained or registered 3D scan patches, wherein said selection is performed during scanning; and
   re-registering one or more 3D scan patches forming part of the digital 3D representation, wherein said re-registering is based on applying one or more transformations to the selected sub-set of scan patches, whereby the accuracy of a digital 3D representation is improved;
   wherein one or more transformations are applied to each 3D scan patch within the sub-set of 3D scan patches, wherein said transformation(s) include translation or rotation; and
   wherein 3D scan patches not forming part of the selected sub-set are transformed according to a weighted average of the transformations applied to one or more scan patches within the sub-set of 3D scan patches.

2. The method according to claim 1, wherein the step of re-registering is performed during scanning.

3. The method according to claim 1, wherein the step of re-registering comprises translating and/or rotating the one or more 3D scan patches relative to each other or relative to the three-dimensional (3D) representation.

4. The method according to claim 1, wherein the step of re-registering one or more 3D scan patches is completed before a new 3D scan patch is obtained.

5. The method according to claim 1, wherein the step of re-registering is completed in less than 1 second.

6. The method according to claim 1, wherein the step of re-registering is completed in less than 200 milliseconds.

7. The method according to claim 1, wherein at least 20 new 3D scan patches are obtained per second.

8. The method according to claim 1, wherein all steps of the method are performed continuously and in real-time.

9. The method according to claim 1, wherein a plurality of 3D scan patches forming part of the digital 3D representation are re-registered during the step of re-registering.

10. The method according to claim 1, wherein all 3D scan patches forming part of the digital 3D representation are re-registered during the step of re-registering.

11. The method according to claim 1, wherein the re-registration of the 3D scan patches is a global registration.

12. The method according to claim 1, wherein the step of re-registering comprises simultaneously applying one or more transformations to a plurality of 3D scan patches, said transformations including translation and/or rotation.

13. A computer system comprising one or more processors configured to perform the steps of the method according to claim 1.

14. A non-transitory computer-readable data carrier having stored thereon a computer program product comprising instructions which, when the program is executed by a computer, cause the computer to carry out the steps of the method according to claim 1.

15. A system for generating a digital three-dimensional representation of a dental object during scanning, the system comprising:
   a dental imaging device comprising:
      one or more projectors configured for illuminating a surface of the dental object during scanning;
      one or more image sensors configured for acquiring sets of two-dimensional (2D) images in response to illuminating said surface; and
      one or more processors configured to perform the steps of the method according to claim 1.

16. The system according to claim 15, wherein the dental imaging device is based on a focus scanning principle.

17. The method according to claim 1, wherein said transformation(s) include translation.

18. The method according to claim 1, wherein said transformation(s) include rotation.

19. The method according to claim 1, wherein said transformation(s) include translation and rotation.

\* \* \* \* \*